United States Patent
Raymond et al.

(10) Patent No.: US 10,500,092 B2
(45) Date of Patent: Dec. 10, 2019

(54) TREATMENT PLANNING METHOD AND SYSTEM FOR CONTROLLING LASER REFRACTIVE SURGERY

(75) Inventors: Thomas D. Raymond, Edgewood, NM (US); Daniel R. Neal, Tijeras, NM (US)

(73) Assignee: AMO WaveFront Sciences, LLC, Santa Ana, CA (US)

( * ) Notice: Subject to any disclaimer, the term of this patent is extended or adjusted under 35 U.S.C. 154(b) by 2027 days.

(21) Appl. No.: 13/341,385

(22) Filed: Dec. 30, 2011

(65) Prior Publication Data

US 2012/0172854 A1 Jul. 5, 2012

Related U.S. Application Data

(60) Provisional application No. 61/428,644, filed on Dec. 30, 2010.

(51) Int. Cl.
*A61F 9/00* (2006.01)
*A61F 9/008* (2006.01)

(52) U.S. Cl.
CPC ...... *A61F 9/008* (2013.01); *A61F 2009/0088* (2013.01); *A61F 2009/00857* (2013.01);
(Continued)

(58) Field of Classification Search
CPC ............ A61F 9/008; A61F 2009/00857; A61F 2009/0088; A61F 2009/00872;
(Continued)

(56) References Cited

U.S. PATENT DOCUMENTS

| 4,669,466 A | 6/1987 | L'Esperance |
| 4,721,379 A * | 1/1988 | L'Esperance ....... A61F 9/00804 351/212 |

(Continued)

FOREIGN PATENT DOCUMENTS

| EP | 1 327 948 B1 | 7/2006 |
| EP | 2232198 B1 | 6/2015 |

(Continued)

OTHER PUBLICATIONS

International Search Report and Written Opinion for Application No. PCT/US2015/062225, dated Aug. 9, 2016, 10 pages.

(Continued)

*Primary Examiner* — Eric D. Bertram
(74) *Attorney, Agent, or Firm* — Johnson & Johnson Surgical Vision, Inc.

(57) ABSTRACT

Improved devices, systems, and methods for diagnosing, planning treatments of, and/or treating the refractive structures of an eye of a patient incorporate results of prior refractive corrections into a planned refractive treatment of a particular patient by driving an effective treatment vector function based on data from the prior eye treatments. The exemplary effective treatment vector employs an influence matrix which may allow improved refractive corrections to be generated so as to increase the overall accuracy of laser eye surgery (including LASIK, PRK, and the like), customized intraocular lenses (IOLs), refractive femtosecond treatments, and the like.

26 Claims, 17 Drawing Sheets

(52) U.S. Cl.
CPC ............... *A61F 2009/00859* (2013.01); *A61F 2009/00872* (2013.01)

(58) Field of Classification Search
CPC ........ A61F 2009/00859; A61F 9/00736; A61F 9/00806; A61F 9/00829; A61F 2009/0087
USPC ................................................ 606/5, 10–13
See application file for complete search history.

(56) References Cited

U.S. PATENT DOCUMENTS

| | | |
|---|---|---|
| 5,777,719 A | 7/1998 | Williams et al. |
| 6,095,651 A | 8/2000 | Williams et al. |
| 6,428,533 B1 | 8/2002 | Bille |
| 6,550,917 B1 | 4/2003 | Neal et al. |
| 6,572,230 B2 | 6/2003 | Levine |
| 6,698,889 B2 | 3/2004 | Pettit et al. |
| 6,908,196 B2 | 6/2005 | Herekar et al. |
| 7,044,944 B2 * | 5/2006 | Campin .............. A61F 9/00806 128/898 |
| 7,455,407 B2 | 11/2008 | Neal et al. |
| 7,553,022 B2 | 6/2009 | Neal et al. |
| 7,980,699 B2 | 7/2011 | Neal et al. |
| 7,988,292 B2 | 8/2011 | Neal et al. |
| 8,126,246 B2 | 2/2012 | Farrer et al. |
| 8,260,024 B2 | 9/2012 | Farrer et al. |
| 8,430,508 B2 | 4/2013 | Weeber |
| 8,444,267 B2 | 5/2013 | Weeber et al. |
| 8,480,228 B2 | 7/2013 | Weeber |
| 8,623,081 B2 | 1/2014 | Canovas et al. |
| 8,696,119 B2 | 4/2014 | Van et al. |
| 8,696,120 B2 | 4/2014 | Van et al. |
| 8,746,882 B2 | 6/2014 | Canovas et al. |
| 2003/0053030 A1 | 3/2003 | Levine |
| 2005/0096640 A1 | 5/2005 | Dai et al. |
| 2005/0254006 A1 * | 11/2005 | Dai ..................... A61B 3/0025 351/159.73 |
| 2006/0173644 A1 | 8/2006 | Dai et al. |
| 2006/0235369 A1 | 10/2006 | MacRae et al. |
| 2007/0142826 A1 | 6/2007 | Sacharoff |
| 2007/0201001 A1 | 8/2007 | Dai |
| 2009/0033867 A1 | 2/2009 | Dai |
| 2009/0161090 A1 | 6/2009 | Campbell et al. |
| 2013/0226294 A1 | 8/2013 | Van et al. |
| 2013/0282116 A1 | 10/2013 | Van et al. |
| 2013/0335701 A1 | 12/2013 | Canovas et al. |
| 2014/0253877 A1 | 9/2014 | Li et al. |

FOREIGN PATENT DOCUMENTS

| | | |
|---|---|---|
| WO | 0158339 A2 | 8/2001 |
| WO | 02/07660 A2 | 1/2002 |
| WO | 03/082162 A2 | 10/2003 |
| WO | 2008112292 A1 | 9/2008 |
| WO | 2008/151111 A1 | 12/2008 |
| WO | 2013028992 A1 | 2/2013 |
| WO | 2013053938 A1 | 4/2013 |
| WO | 2014172621 A2 | 10/2014 |

OTHER PUBLICATIONS

International Search Report and Written Opinion for Application No. PCT/US2011/068169, dated Apr. 18, 2012, 16 pages.

Koh S., et al., "Simultaneous Measurement of Tear Film Dynamics Using Wave front Sensor and Optical Coherence Tomography," Investigative Ophthalmology & Visual Science, 2010, vol. 51 (7), pp. 3441-3448.

Kottig F., et al., "An Advanced Algorithm for Dispersion Encoded Full Range Frequency Domain Optical Coherence Tomography," Optics Express, 2012, vol. 20 (22), pp. 24925-24948.

Liu H., et al., "Measurement of the Time Course of Optical Quality and Visual Deterioration during Tear Break-Up," Investigative Ophthalmology & Visual Science, 2010, vol. 51 (6), pp. 3318-3326.

Mejia-Barbosa Y., et al., "Object Surface for Applying a Modified Hartmann Test to Measure Corneal Topography," Applied Optics, 2001, vol. 40 (31), pp. 5778-5786.

Partial International Search Report for Application No. PCT/US2015/065713, dated Apr. 14, 2016, 9 pages.

Wojtkowski M., et al., "Full Range Complex Spectral Optical Coherence Tomography Technique in Eye Imaging," Optics Letters, 2002, vol. 27 (16), pp. 1415-1417.

Nowakowski, M., et al., "Investigation of the isoplanatic patch and wavefront aberration along the pupillary axis compared to the line of sight in the eye," Biomedical Optics Express, Feb. 1, 2012, pp. 240-258, vol. 3, No. 2.

Yang, S., et al., "Neural network computer program to determine photorefractive keratectomy nomograms," Journal of Cataract & Refractive Surgery, Jul. 1998, pp. 917-924, vol. 24, No. 7.

Zou, W., et al., "High-accuracy wavefront control for retinal imaging with Adaptive-Influence-Matrix Adaptive Optics," Optics Express, Oct. 26, 2009, pp. 20167-20177, vol. 17, No. 22.

\* cited by examiner

TREATMENT PLANNING METHOD AND SYSTEM FOR CONTROLLING LASER REFRACTIVE SURGERY

CROSS REFERENCE TO RELATED APPLICATION DATA

The present application is a nonprovisional of, and claims the benefit under 35 USC 119(e) of, U.S. Provisional Application No. 61/428,644 filed Dec. 30, 2010, the full disclosure of which is incorporated herein by reference in its entirety.

BACKGROUND OF THE INVENTION

The present invention pertains generally to ophthalmic surgery and diagnosis, particularly for identification and/or correction of optical vision deficiencies. In exemplary embodiments, the present invention provides systems and methods for planning and implementing refractive corrections in an eye of a patient, with the corrections optionally being performed using lasers.

Corneal shape corrective surgeries are commonly used to treat myopia, hyperopia, astigmatism, and the like. Laser refractive procedures include LASIK and (Laser Assisted In-Situ Keratomileusis), Photorefractive Keratectomy (PRK), Epithelial Keratomileusis (LASEK or Epi-LASEK), Laser Thermal Keratoplasty, and the Alternative refraction altering procedures which do not rely on lasers, and/or which do not alter the corneal shape, have also been described.

During LASIK, a surgeon makes a cut part way through a front surface of a cornea, optionally using an oscillating steel blade or microkeratome. The microkeratome automatically advances the blade through the cornea so as to create a thin flap of clear tissue on the front central portion of the eye. The flap can be folded over to expose stromal tissue for selective ablation with an excimer laser. More recently, femtosecond laser systems have been developed to form laser incision in the corneal tissue so as to cut the corneal flap without use of a mechanical blade. Regardless, the excimer laser is programmed to correct a visual defect by directing a beam of pulsed laser energy onto the exposed stroma. Each pulse removes a very small and precise amount of corneal tissue so that the total removal of stromal tissue from within the cornea alters and corrects the refractive properties of the overall eye. After removal (and more specifically, after laser ablation) of the desired stromal tissue, the flap can be folded back over the ablated surface. The flap of protective epithelial tissue quickly and naturally reattaches over the resculpted stromal tissue, and the eye retains much of the effective alteration in shape after corneal healing.

A number of alternative laser refractive procedures have been used and/or are being developed. In one variation, rather than incising the corneal tissue for temporary displacement of an epithelial flap, the epithelium may be ablated (typically using the excimer laser) or abraded in a PRK procedure. As an alternative to resculpting the stroma using an excimer laser, it has also been proposed to form incisions within the cornea or other refractive tissues of the eye with the femtosecond laser. Still further alternatives have been described, and new procedures are being developed to further enhance the capabilities of refractive corrections using lasers and other refractive tissue altering tools.

Known corneal correction treatment methods have generally been quite successful in correcting standard vision errors, such as myopia, hyperopia, and astigmatism. However, as with all successes, still further improvements have become desirable. Toward that end, wavefront measurement systems are now available to measure the refractive characteristics of a particular patient's eye. These wavefront measurement systems allow accurate diagnosis of the overall aberrations of the optical system of the eye, providing quite detailed information on the high-order optical aberrations that may limit a patient's visual acuity even after the standard refractive errors have been corrected (for example, by eye glasses, contact lenses, and the like). Still additional diagnostic tools may provide information which is useful for such customized ablation procedures. For example, corneal topographers are commercially available that can provide quite accurate information regarding the shape of the anterior surface of the cornea, and this surface may have a significant role in the overall optical properties of the eye. Optical coherence tomographers (OCT) may provide information regarding both the anterior and interior surfaces of the eye. By combining these accurate diagnostic tools with the flexibility of modern scanning excimer lasers, custom refractive corrections should correct not only the standard refractive errors of the eye, but also address the specific high-order aberrations of a particular patient.

Although customized laser and other refractive treatments have provided significant benefits for many patients, the overall improvement in refractive performance of the eyes of patients treated using these new techniques has not yet achieved their full theoretical potential. A number of theories or factors have been proposed to help explain why some customized ablation procedures have not altogether eliminated high-order aberrations of the eye. Even when laser refractive corrections were limited to the standard refractive errors of myopia, hyperopia, and astigmatism, the empirical response of prior treatments led to doctors applying discrete adjustment factors or "nomograms" so as to adjust a calculated prescription before imposing the treatment on an eye of a patient. Significant efforts have gone toward increasing the benefit of both standard and customized refractive corrections by identifying analogous nomogram adjustments for high-order aberration corrections. Unfortunately, work in connection with the present invention indicates the challenges of identifying suitable nomogram adjustments for a customized refractive correction for a particular patient in a particular treatment setting may continue to limit the benefits of customized corneal ablations to significantly less than the ideal potential outcomes. In fact, a significant number of high-order refractive treatments may result in other high-order aberrations of the eye actually increasing (even where the visual acuity of the eye overall benefits from the treatment).

In light of the above, it would be beneficial to provide improved devices, systems, and methods for diagnosing and/or treating refractive defects of an eye of a patient. Preferably, these improved techniques would still allow physicians to input nomogram adjustments for a particular patient. It would be particularly beneficial if these improvements were able to increase the overall accuracy with which high-order aberrations of an eye could be treated, ideally without significantly increasing the cost or complexity of diagnostic and/or treatment systems.

BRIEF SUMMARY OF THE INVENTION

The present invention generally provides improved devices, systems, and methods for diagnosing, planning treatments of, and/or treating the refractive structures of an eye of a patient. The present invention provides a holistic approach for incorporating results of prior refractive corrections into a planned refractive treatment of a particular patient by deriving an effective treatment vector function based on data from the prior eye treatments. This effective treatment vector function represents a multivariate feedback approach that can accommodate a large number of factors which contribute to the accuracy of LASIK corrections and other refractive treatments. The exemplary effective treatment vector function employs an influence matrix analytical approach. Although many factors can contribute to induced errors, often with complex couplings between the factors and discrete optical error modes, the use of an influence matrix, (along with a relatively large number of prior eye treatments) may allow improved refractive corrections to be generated from the aberration measurement techniques that are now available. Appropriate use of an influence matrix or other effective treatment vector functions may thereby increase the overall accuracy of laser eye surgery (including LASIK, PRK, and the like), customized intraocular lenses (IOLs), refractive femtosecond treatments, and the like. The holistic approach and system described herein can provide surprising improvements in optical therapies and treatment planning.

In a first aspect, the invention provides a method for planning a refractive treatment of an eye of a patient. The method comprises determining an effective treatment vector function based on a plurality of prior eye treatments. The effective treatment vector function may be determined by, for each prior eye treatment of an associated eye, defining a pre-treatment vector that characterizes measured pre-treatment high-order aberrations of that eye. A post treatment vector characterizing measured post treatment high-order aberrations of the eye is also defined. The effective treatment vector function can then be determined by deriving a correlation between the pre-treatment vectors and the associated post-treatment vectors. An input vector for a particular patient may be defined based on measured pre-treatment, high-order aberrations of the eye of the patient, and the treatment of the eye of the patient may be derived by applying the effective treatment vector function to the input vector.

The input vector may be defined by identifying a target refraction of the eye of the patient to be induced by the refractive treatment. In many cases, the target refraction for the eye of the patient may be emmetropia, such that after treatment of the patient's eye the aberrations are substantially eliminated. Note that his will not always be the case, as treatments may intentionally induce certain desirable aberrations into the eye so as to mitigate presbyopia and the like. Regardless, once the target refraction has been identified, an intended refractive correction vector (IRC) characterizing a difference between the measured pre-treatment aberrations of the eye of the patient and the target can then be determined.

The deriving of the effective treatment vector function may be performed by determining intended refractive correction vectors for each (IRCs) of the associated eyes. A surgically-induced refractive correction (SIRC) can be defined for each eye as the actual change in aberrations, for example, with each SIRC characterizing a difference between the measured pre-treatment aberrations and the pot-treatment aberrations of the associated eye.

In the exemplary embodiments, the effective treatment vector function may be derived by determining an influence matrix $\vec{f}$ relating the SIRCs to the IRCs. For example, $\vec{f}$ may relate the SIRCs to the IRCs such that, for the group of associated eyes:

$$\vec{E} = \overrightarrow{SIRC} - \vec{f} \bullet \overrightarrow{IRC} \qquad \text{Eq. 1}$$

in which $\vec{E}$ is an error vector (which can be driven toward zero so as to derive f). The effective treatment vector function may be applied to the input vector by calculating an adjusted intended refractive correction vector (AIRC) from a vector IRC for the eye of the patient which can (in turn) optionally be defined by adjusting the IRC per a physician adjustment and/or a nomogram adjustment. The IRC' (or a vector derived therefrom) can be used as the input vector for deriving the AIRC, and/or for deriving the treatment of the eye of the patient, thereby allowing physician adjustments and nomogram adjustments when desired.

Preferably, the effective treatment vector function is derived using an influence matrix approach. More specifically, the planned treatment of the eye of the patient may be characterized by a planned treatment matrix, and the influence matrix may be derived such that a plurality of the elements of the input vector each alter a plurality of elements of the planned treatment vector. Similarly, a plurality of the planned treatment vector elements may each be altered by a plurality of elements of the input vector. In fact, the influence matrix may be derived such that every element of the input vector (at least those characterizing a refractive shape of the eye of the patient) can and/or does alter every element of the planned treatment matrix (or at least those characterizing a change in the refractive shape of the eye of the patient).

The pre-treatment aberration measurements of the input vector will typically characterize refractive aspects of the eye of the patient, including refractive (such as the standard refractive characteristics of spherical error, astigmatism power, and astigmatism angle) and high-order aberrations (such as Zernike coefficients or the like) of the eye. The input vector may also characterize non-refractive cofactors, including characteristics of the patient (such as the patient's age, gender, race, and the like) and/or the treatment settings (such as the identity of the physician or other system user, the type or specific system used for diagnosis and/or treatment, the humidity during diagnosis and/or treatment, the temperature during diagnosis and/or treatment, the geographical location of diagnosis and/or treatment, and the like.) The pre-treatment vectors and post-treatment vectors for the prior eye treatments (from which the influence matrix will be derived) may include similar elements.

An exemplary method for deriving the treatment of the eye of the patient may be to multiply the influence matrix of the effective treatment vector function by the input vector so as to define a conditioned input vector. A refractive treatment may be planned using matrix elements of the conditioned input vector.

In another aspect, the invention provides a method for planning a refractive treatment of an eye of a patient. The method comprises deriving an influence matrix from a plurality of prior eye treatments. For a particular eye and an associated particular treatment, an intended refractive correction vector (IRC) may be determined, with the IRC characterizing a difference between measured pre-treatment high-order aberrations and a target refraction. Similar IRC vectors may be prepared for each of the prior eye treatments. A surgically induced refractive correction vector (SIRC) may similarly be determined for each previously treated eye, with each SIRC characterizing a difference between the measured pre-treatment aberrations and measured post-treatment aberrations of that eye. The influence matrix can then be derived so as to provide a correlation between the IRCs and the SIRCs. A patient IRC vector can be defined characterizing a difference between measured pre-treatment high-order aberrations of the eye of the patient, and a target refraction of the eye of the patient. The patient IRC vector can then be adjusted to produce an adjusted IRC based on the influence matrix. In many embodiments, the patient will be treated based on the adjusted IRC.

In another aspect, the invention provides a method for planning a refractive treatment of an eye of a patient. An influence matrix will preferably have been derived from a plurality of prior eye treatments. The influence matrix may be derived by determining a target refraction of each eye along with an intended refractive correction vector (IRC) characterizing a difference between pre-treatment high-order aberrations and the target. A surgically induced refraction correction vector (SIRC) will also be determined for each eye, with the SIRC characterizing a difference between the measured pre-treatment aberrations and measured post-treatment aberrations. The influence matrix will be derived so as to provide a correlation between the IRCs and the SIRCs. The method comprises receiving a patient IRC vector characterizing a difference between measured pre-treatment high-order aberrations of the eye of the patient and a target refraction of the eye of the patient. The IRC vector is adjusted based on the influence matrix. In many embodiments, the patient will then be treated based on the adjusted IRC.

In another aspect, the invention provides a system for planning a refractive treatment of an eye of a patient. The system comprises an input for receiving pre-treatment high-order aberrations of the eye of the patient. A processor is coupled to the input. The processor derives the treatment of the eye of the patient in response to the high-order aberrations of the eye of the patient by applying an effective treatment vector function. The effective treatment vector function is derived from the correlation between pre-treatment vectors characterizing high-order aberrations and post-treatment vectors characterizing post-treatment high-order aberrations for each of a plurality of previously treated eyes. An output is coupled to the processor so as to transmit the treatment to facilitate improving refraction of the eye of the patient.

The processor will often comprise software in the form of tangible media embodying machine readable instructions for deriving the treatment. In exemplary embodiments, the processor is configured to generate and/or store an input vector for the eye of the patient in response to a target refraction that is desired to be induced by the treatment. The input vector can be generated by determining an intended refractive correction vector (IRC) characterizing a difference between pre-treatment measured aberrations of the eye and the target. Exemplary embodiments may include one or more aberrometer (such as a wavefront sensor) coupled to the input. The processor may be configured to derive the effective treatment vector function from a plurality of prior treatments using intended refractive correction vectors (IRCs) of the associated eyes to determine surgically induced refraction correction vectors (SIRCs) of the associated eyes, with each SIRC characterizing a difference between the measured pre-treatment aberrations and the post-treatment aberrations of the associated eye. Particularly preferred embodiments derive the effective treatment vector function using an influence matrix $\vec{T}$ relating the SIRCs to the IRCs. $\vec{T}$ can be derived such that for the associated eyes:

$$\vec{E} = \overrightarrow{SIRC} - \vec{T} \cdot \overrightarrow{IRC}$$

in which $\vec{E}$ is an error vector. The effective treatment function can be applied to the input vector by calculating an adjusted intended refractive correction vector (AIRC) such that:

$$\overrightarrow{AIRC} = \vec{T}^{-1} \bullet \overrightarrow{IRC'}$$

in which $\vec{T}^{-1}$ is an inverse of $\vec{T}$, and in which IRC' is based on the IRC of the eye of the patient (optionally so as to incorporate physician input, nomograms, and/or the like). Advantageously, the processor may have an input for receiving physician adjustments to the IRC, nomogram adjustments to the IRC, and/or the like. The processor can define an IRC' for the eye of the patient by applying, to the IRC of the eye of the patient, these adjustments. The input vector can then be based on the IRC'.

Typically, the effective treatment vector function is based on an influence matrix. The planned treatment of the eye will typically comprise a planned treatment vector, and a plurality of the elements of the input vector can each alter a plurality of elements of the planned treatment vector. In other embodiments, a plurality of the planned treatment vector elements may each be altered by a plurality of the elements of the input vector. In fact, all of the refractive elements of the input vector may impact every element of the planned treatment vector through use of the exemplary influence matrix derivation approach.

In another aspect, the invention provides a system for planning a refractive treatment of an eye of a patient. The system comprises a processor having an input for receiving data regarding a plurality of prior eye treatments. The processor is configured so as to derive an influence matrix from the prior eye treatment data. The influence matrix may be derived by determining an intended refractive correction vector (IRC) characterizing a difference between measured pre-treatment high-order aberrations and target refractions of each eye associated with a prior eye treatment. A surgically induced refraction correction vector (SIRC) of each eye is determined by characterizing a difference between the measured pre-treatment aberrations and measured post-treatment aberrations, with a vector being determined for each associated eye. The influence matrix will generally comprise a correlation between the IRCs and the SIRCs. The system has an input for receiving a patient IRC vector characterizing a difference between measured pre-treatment high-order aberration of the eye of the patient and a target refraction of the eye of that patient. An output is coupled to the processor for transmitting a treatment. The processor is configured to derive the treatment by adjusting the patient IRC vector based on the influence matrix.

In yet another aspect, the invention provides a system for planning a refractive treatment of an eye of the patient. An influence matrix will have been derived from a plurality of prior eye treatments. The influence matrix is derived by, for each prior eye treatment of an associated eye, determining a target refraction of the associated eye along with an intended refractive correction vector characterizing the difference between measured pre-treatment high-order aberrations of the associated eye and the target. A surgically induced refraction correction vector (SIRC) is also determined for each eye, with the SIRC characterizing a difference between measured pre-treatment aberrations and measured post-treatment aberrations of that eye. The influence matrix is derived so as to provide a correlation between the IRCs and the SIRCs. The system comprises an input for receiving a patient IRC vector characterizing a difference between measured pre-treatment high-order aberrations of the eye of the patient and a target refraction of the eye of the patient. A processor is coupled to the input. The processor is configured for adjusting the patient IRC vector based on the influence matrix. Optionally, the adjusted IRC vector may be output to a high-order refraction correcting apparatus, such as a laser eye surgery system, the custom IOL lens fab system, a refractive femtosecond laser system, or the like.

In one aspect, embodiments of the present invention encompass methods for planning a refractive treatment of an eye of a patient. Exemplary methods may include determining an effective treatment vector function based on a plurality of prior eye treatments by, for each prior eye treatment of an associated eye, defining a pre-treatment vector characterizing measured pre-treatment optical properties of the associated eye, defining a post-treatment vector characterizing measured post treatment optical properties of the associated eye, and deriving the effective treatment vector function using a correlation between the pre-treatment vectors and the post-treatment vectors. Methods may also include defining an input vector based on measured pre-treatment optical properties of the eye of the patient, and deriving the treatment of the eye of the patient by applying the effective treatment vector function to the input vector. In some cases, the measured pre-treatment optical properties include a member selected from the group consisting of a low order aberration, a high order aberration, a corneal topography measurement, an optical coherence tomography measurement, and a corneal keratometry value. In some cases, the refractive treatment includes a member selected from the group consisting of an excimer laser treatment, a femtosecond laser treatment, an intraocular lens treatment, a contact lens treatment, and a spectacle treatment. In some cases, the process of defining the input vector includes identifying a target refraction of the eye of the patient to be induced by the refractive treatment, and determining an intended refractive correction vector (IRC) characterizing a difference between the measured pre-treatment aberrations of the eye of the patient and the target. The process of deriving the effective treatment vector function from prior treatments may include determining intended refractive correction vectors (IRCs) of the associated eyes, and determining surgically induced refractive correction vectors (SIRCs) of the associated eyes, where each SIRC characterizes a difference between the measured pre-treatment aberrations and the post-treatment aberrations of an associated eye. In some cases, the process of deriving the effective treatment vector function includes determining an influence matrix relating the SIRCs to the IRCs. In some cases, methods may include defining an IRC' for the eye of the patient by applying, to the IRC of the eye of the patient, at least one adjustment selected from the group consisting of physician adjustments to the IRC, and nomogram adjustments to the IRC. The input vector can be based on the IRC'. In some cases, the effective treatment vector function may be derived using an influence matrix. In some cases, the planned treatment of the eye of the patient is characterized by a planned treatment vector, and the influence matrix is derived such that a plurality of the elements of the input vector each alter a plurality of elements of the planned treatment vector. In some cases, the planned treatment of the eye of the patient is characterized by a planned treatment vector, and the influence matrix is derived such that a plurality of the planned treatment vector elements are each altered by a plurality of elements of the input vector. In some cases, the planned treatment of the eye of the patient is characterized by a planned treatment vector, and the influence matrix is derived such that every element of the input vector characterizing a refractive shape of the eye of the patient can alter every element of the planned treatment vector characterizing a change in the refractive shape of the eye of the patient. In some cases, the pre-treatment vectors and the input vector characterize refraction, non-refractive cofactors characterizing the patient and/or the treatment setting, and the optical properties of the eyes. In some cases, the treatment of the eye of the patient is derived by multiplying the influence matrix of the effective treatment vector function by the input vector so as to define a conditioned input vector, and by planning a refractive treatment with matrix elements of the conditioned input vector.

In another aspect, embodiments of the present invention encompass methods for planning a refractive treatment of an eye of a patient. Exemplary methods may include deriving an influence matrix from a plurality of prior eye treatments by, for each prior eye treatment of an associated eye, determining an intended refractive correction vector (IRC) characterizing a difference between measured pre-treatment high-order aberrations of the associated eye and a target refraction of the associated eye, and determining a surgically induced refractive correction vector (SIRC) of the associated eye characterizing a difference between the measured pre-treatment aberrations and measured post-treatment aberrations of the associated eye. The influence matrix can be derived so as to provide a correlation between the IRCs and the SIRCs. Methods may also include defining a patient IRC vector characterizing a difference between measured pre-treatment high-order aberrations of the eye of the patient and a target refraction of the eye of the patient, and adjusting the patient IRC vector based on the influence matrix. In some cases, for each prior eye treatment of the associated eye, the IRC can be further determined so as to characterize a difference between measured pre-treatment low order aberrations and target low order aberrations, and so as to characterize a difference between measured pre-treatment corneal topography and target corneal topography, and the SIRC is further determined so as to characterize a difference between the measured pre-treatment low order aberrations and measured post-treatment aberrations, and so as to characterize a difference between measured the pre-treatment corneal topography and measured post-treatment corneal topography. The patient IRC vector can be further defined so as to characterize a difference between measured pre-treatment low order aberrations and the target refraction, and so as to characterize a difference between measured pre-treatment topography of the eye and target topography. In some cases, methods may include treating the patient based on the adjusted IRC.

In another aspect, embodiments of the present invention encompass methods for planning a refractive treatment of an eye of a patient. An influence matrix may have been derived from a plurality of prior eye treatments by, for each prior eye treatment of an associated eye, determining a target refraction of the associated eye, determining an intended refractive correction vector (IRC) characterizing a difference between measured pre-treatment optical properties of the associated eye and the target, and determining a surgically induced refractive correction vector (SIRC) of the associated eye characterizing a difference between the measured pre-treatment optical properties and measured post-treatment optical properties of the associated eye. The influence matrix can be derived so as to provide a correlation between the IRCs and the SIRCs. Methods may include receiving a patient IRC, vector characterizing a difference between measured pre-treatment optical properties of the eye of the patient and a target refraction of the eye of the patient, and adjusting the patient IRC vector based on the influence matrix.

In still another aspect, embodiments of the present invention encompass systems for planning a refractive treatment of an eye of a patient. Exemplary systems may include an input for receiving pre-treatment optical properties of the eye of the patient, and a processor coupled to the input, the processor deriving the treatment of the eye of the patient in response to the optical properties of the eye of the patient by applying an effective treatment vector function. The effective treatment vector function can be derived from, for each of a plurality of prior eye treatments, a correlation between a pre-treatment vector characterizing optical properties of the associated eye before treatment, and a post-treatment vector characterizing post-treatment optical properties of the associated eye. Systems can also include an output coupled to the processor so as to transmit the treatment to facilitate improving refraction of the eye of the patient. In some cases, the pre-treatment optical properties of the eye of the patient can include at least one member selected from the group consisting of a low order aberration, a high order aberration, a corneal topography measurement, an optical coherence tomography measurement, and a corneal keratometry value. In some cases, for each of the plurality of prior eye treatments, the pre-treatment vector can characterize optical properties of the associated eye before treatment, and the optical properties may include one or more member selected from the group consisting of a low order aberration, a high order aberration, a corneal topography measurement, an optical coherence tomography measurement, and a corneal keratometry value. In some cases, the post-treatment vector may characterize optical properties of the associated eye before treatment, and the optical properties may include one or more member selected from the group consisting of a low order aberration, a high order aberration, a corneal topography measurement, an optical coherence tomography measurement, and a corneal keratometry value. In some cases, the output is configured to facilitate a refractive treatment including a member selected from the group consisting of an excimer laser treatment, a femtosecond laser treatment, an intraocular lens treatment, a contact lens treatment, and a spectacle treatment. In some cases, the processor includes tangible media embodying machine readable instructions for implementing the derivation of the treatment. In some cases, the processor is configured to generate an input vector for the eye of the patient in response to a target refraction of the eye of the patient to be induced by the refractive treatment by determining an intended refractive correction (IRC) characterizing a difference between measured pre-treatment aberrations of the eye of the patient and the target. In some cases, systems may include an aberrometer coupled to the input, the aberrometer sensing the low order aberrations of the eye and the high-order aberrations of an eye and transmitting the low and high-order aberrations to the processor. In some cases, the aberrometer is configured to sense corneal topography and to transmitting the corneal topography to the processor. In some cases, systems may include an optical coherence tomography measurement apparatus coupled to the input, the optical coherence tomography measurement apparatus sending the optical properties of an eye and transmitting the optical properties to the processor. In some cases, systems may include a keratometry apparatus coupled to the input, the keratometry apparatus sensing the optical properties of an eye and transmitting the optical properties to the processor. In some cases, the processor can be configured to derive the effective treatment vector function from prior treatments in response to intended refractive correction vectors (IRCs) of the associated eyes and to determine surgically induced refractive correction vectors (SIRCs) of the associated eyes, each SIRC characterizing a difference between the measured pre-treatment aberrations and the post-treatment aberrations of an associated eye. In some cases, the effective treatment vector function can be based on an influence matrix relating the SIRCs to the IRCs. In some cases, systems may include an additional input coupled to the processor for receiving at least one adjustment selected from the group consisting of physician adjustments to the IRC, and nomogram adjustments to the IRC. The processor can be configured to define an IRC' for the eye of the patient by applying, to the IRC of the eye of the patient, the at least one adjustment, the input vector being based on the IRC'. In some cases, the effective treatment vector function can be based on an influence matrix. In some cases, the planned treatment of the eye of the patient may include a planned treatment vector, and a plurality of the elements of the input vector may each alter a plurality of elements of the planned treatment matrix, and/or a plurality of the planned treatment vector elements may each be altered by a plurality of elements of the input vector. In some cases, an input vector includes refractive elements characterizing refraction of the eye of the patient, non-refractive cofactors characterizing the patient and/or the treatment setting, and elements characterizing the optical properties of the eye. In some cases, elements characterizing the optical properties of the eye can include a member selected from the group consisting of a high order element characterizing a high order aberration of the eye, a low order element characterizing a low order aberration of the eye, a corneal topography measurement element characterizing a corneal topography measurement of the eye, an optical coherence tomography measurement element characterizing an optical coherence topography measurement of the eye, and a corneal keratometry value element characterizing a corneal keratometry value of the eye. In some cases, a processor can be configured to derive the treatment of the eye of the patient by multiplying the influence matrix of the effective treatment vector function by the input vector.

In yet another aspect, embodiments of the present invention encompass systems for planning a refractive treatment of an eye of a patient. Exemplary systems may include a processor having an input for receiving data regarding a plurality of prior eye treatments and for deriving an influence matrix therefrom by, for each prior eye treatment of an associated eye, determining an intended refractive correction vector (IRC) characterizing a difference between measured pre-treatment high-order aberrations of the associated eye and a target refraction of the associated eye, and determining a surgically induced refractive correction vector (SIRC) of the associated eye characterizing a difference between the measured pre-treatment aberrations and measured post-treatment aberrations of the associated eye. In some cases, the influence matrix can include a correlation between the IRCs and the SIRCs. In some cases, systems may also include another input for receiving a patient IRC vector characterizing a difference between measured pre-treatment high-order aberrations of the eye of the patient and a target refraction of the eye of the patient. In some cases, systems may also include an output coupled to the processor for transmitting a treatment, the processor configured to derive the treatment by adjusting the patient IRC vector based on the influence matrix. In some cases, pre-treatment optical properties of the eye of the patient can include at least one member selected from the group consisting of a low order aberration, a high order aberration, a corneal topography measurement, an optical coherence tomography measurement, and a corneal keratometry value. In some cases, for each of the plurality of prior eye treatments, the pre-treatment vector may characterize optical properties of the associated eye before treatment, and the optical properties may include one or more member selected from the group consisting of a low order aberration, a high order aberration, a corneal topography measurement, an optical coherence tomography measurement, and a corneal keratometry value. In some cases, a post-treatment vector may characterize optical properties of the associated eye before treatment. Optical properties may include one or more member selected from the group consisting of a low order aberration, a high order aberration, a corneal topography measurement, an optical coherence tomography measurement, and a corneal keratometry value. In some cases, measured pre-treatment optical properties of the eye of the patient may include a member selected from the group consisting of a low order aberration, a high order aberration, a corneal topography measurement, an optical coherence tomography measurement, and a corneal keratometry value. In some cases, a refractive treatment may include a member selected from the group consisting of an excimer laser treatment, a femtosecond laser treatment, an intraocular lens treatment, a contact lens treatment, and a spectacle treatment. In some cases, systems may also include a laser eye surgery apparatus coupled to the output, where the surgery apparatus generates a laser beam for treating the patient based on the adjusted IRC.

In another aspect, embodiments of the present invention encompass systems for planning a refractive treatment of an eye of a patient. An influence matrix may have been derived from a plurality of prior eye treatments by, for each prior eye treatment of an associated eye, determining a target refraction of the associated eye, determining an intended refractive correction vector (IRC) characterizing a difference between measured pre-treatment optical properties of the associated eye and the target, and determining a surgically induced refractive correction vector (SIRC) of the associated eye characterizing a difference between the measured pre-treatment aberrations and measured post-treatment aberrations of the associated eye. The influence matrix may also be derived so as to provide a correlation between the IRCs and the SIRCs. The system may include an input for receiving a patient IRC vector characterizing a difference between measured pre-treatment optical properties of the eye of the patient and a target refraction of the eye of the patient. In some cases, the system may include a processor coupled to the input, where the processor is configured for adjusting the patient IRC vector based on the influence matrix. In some cases, the measured pre-treatment optical properties of the associated eye may include a member selected from the group consisting of a low order aberration, a high order aberration, a corneal topography measurement, an optical coherence tomography measurement, and a corneal keratometry value. In some cases, the measured pre-treatment optical properties of the eye of the patient may include a member selected from the group consisting of a low order aberration, a high order aberration, a corneal topography measurement, an optical coherence tomography measurement, and a corneal keratometry value. In some cases, the refractive treatment may include a member selected from the group consisting of an excimer laser treatment, a femtosecond laser treatment, an intraocular lens treatment, a contact lens treatment, and a spectacle treatment. In some cases, the influence matrix can be based on a correlation between a pre-treatment cylinder value, a post-treatment sphere value, and a pre-treatment keratometry value of the associated eye. In some cases, the influence matrix can be based on a correlation between a pre-treatment keratometry value of the associated eye and a high order aberration of the associated eye, for example a pre-treatment high order aberration, or a post-treatment aberration.

In yet another aspect, embodiments of the present invention encompass systems for planning a treatment of an eye of a patient having an eye with a natural lens. Exemplary systems may include an input for receiving pre-treatment optical properties of the eye of the patient with the natural lens, and a processor coupled to the input, where the processor derives the treatment of the eye of the patient in response to the optical properties of the eye of the patient by applying an effective treatment vector function, where the effective treatment vector function is derived from, for each of a plurality of prior eye treatments, a correlation between a pre-treatment vector characterizing optical properties of the associated eye with an associated lens therein, and a post-treatment vector characterizing post-treatment optical properties of the associated eye after removal of the natural lens and implantation of an associated intraocular lens. Systems may also include an output coupled to the processor so as to transmit the treatment to facilitate improving refraction of the eye of the patient.

In one aspect, embodiments of the present invention encompass systems for treating an eye of a patient, where the eye has an anterior surface. Exemplary systems may include an input for receiving pre-treatment optical properties of the eye of the patient, and a processor coupled to the input. The processor can be configured to derive the treatment of the eye of the patient in response to the optical properties of the eye of the patient by applying an effective treatment vector function, where the effective treatment vector function is derived from, for each of a plurality of prior eye treatments, a correlation between a pre-treatment vector characterizing optical properties of the associated eye before treatment, and a post-treatment vector characterizing post-treatment optical properties of the associated eye. Systems may also include a femtosecond laser system coupled to the processor so as to focus a pattern of femtosecond laser energy through the anterior surface of the eye of the patient such that the refractive treatment is effected within the eye of the patient.

DETAILED DESCRIPTION OF THE INVENTION

Figure 1:
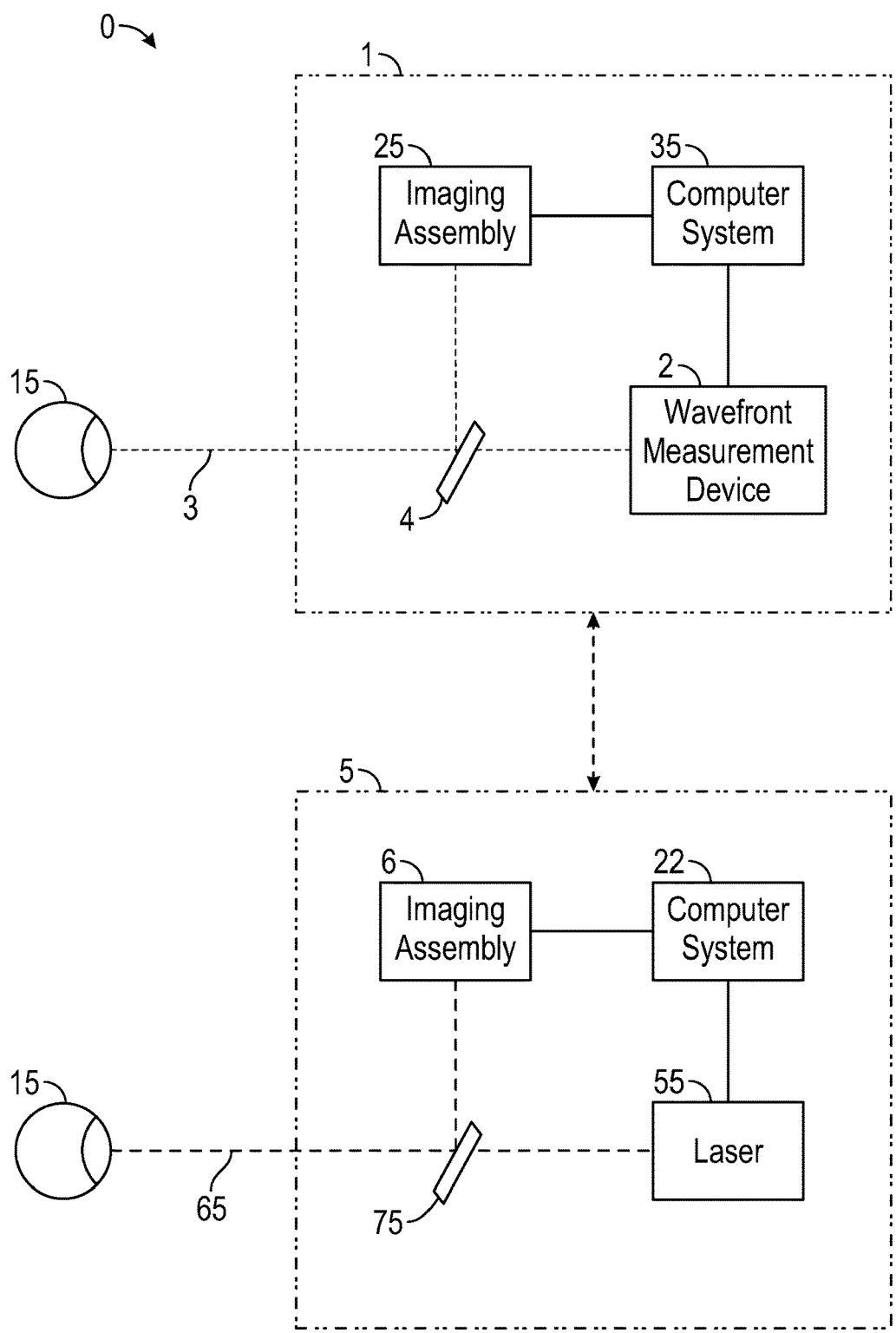
FIG. 1 schematically illustrates a system and method for measurement and treatment of refractive defects of an eye of a patient.

The present invention generally provides improved devices, systems, and methods for diagnosing, planning treatments of, and/or treating the refractive structures of an eye of a patient. Exemplary embodiments of the invention make use of recent developments in diagnosis of refractive properties of the eye, and particularly the tools now available (and/or now being developed) to identify and characterize high-order aberrations of the eye of human patients. Along with the now widely used Hartmann-Shack and other wavefront sensors used to measure aberrations throughout the optical system of the eye, the diagnostic data and systems employed by embodiments of the invention may include topography, pachymetry, pupilometry, keratometry, refractometry, biometry, and/or the like. The optical tissue treatment modalities employed by the methods and systems described herein will often include ablative laser treatments (typically with an excimer or solid-state laser), but may alternatively employ intra-tissue photoaltering technologies such as intrastromal femtosecond laser treatments to form incisions so as to alter the shape of the cornea, or the like. Still further alternative therapies may be directed to altering the effective shape or function of optical tissues of the eye other than the cornea, such as by altering or replacing the lens, altering the structure of the capsular bag, and the like. Hence, a wide variety of diagnostic and/or treatment modalities may be employed in various embodiments of the invention.

Embodiments of the inventions described herein will go beyond prior attempts to identify and characterize specific couplings between optical refractive treatment shapes and potential inducement of an associated high-order aberration. Exemplary embodiments may identify and accurately characterize complex cross-relationships between pre-treatment refractive error modes of the eye and related post-prescriptive shape modifications that enhance overall viewing capabilities of a patient. These aberration/treated eye inter-mode relationships may be, at least in part, specific to an eye treatment modality (such as to ablative resculpting of the eye with a laser eye surgery system), specific to a particular treatment implementation hardware structure (for example, to a specific excimer laser geometry and assembly design, optical train, scanning mechanism, or the like) or even to a specific treatment controlling software package (such as to a shot-pattern generating software package which identifies excimer laser shots so as to produce an approximation to the desired overall refractive resculpting treatment shape). The couplings may also relate to healing effects of the eye, so that compensation for aberration/treated eye couplings may benefit from prior experience with the gradual changes in the tissues that take place in the hours, weeks, and/or ideally months after the treatment is completed.

So as to more effectively gauge and characterize the actual effect of an overall prescription, embodiments of the invention will often make use of measurements from a number of different prior treatments. Preferably, the prior treatments will have employed measurement and/or treatment systems sharing common components, technologies, and the like with the refractive treatment to be planned on a particular patient's eye. In many cases, at least some of the prior treatments from which information will be derived may have been diagnosed and/or treated with treatment components, techniques, and/or under circumstances which differ from those of the refractive treatment to be planned. Nonetheless, by gathering accurate data from the prior treatments, the overall accuracy of the treatment to be planned may be enhanced. More specifically, along with obtaining accurate pre-treatment data characterizing the eyes, embodiments of the methods and systems described herein will benefit significantly from high-order aberration measurements obtained after the treatment of a plurality of eyes, with the post-treatment data ideally being obtained a sufficient time after the treatment has been imposed so as to allow the eye to substantially stabilize and refraction-altering healing response of the treated tissues to substantially terminate. Vector analysis of the pre-treatment high-order aberration measurements and the post-treatment high-order aberration measurements, ideally using an influence matrix approach, allows complex couplings between intended refractive treatments and the overall effective refractive treatments to be identified and used for the future planned treatment of a particular patient's eye.

Along with the pre-treatment measurements and the post-treatment measurements, a variety of co-factors may also be included in the vector analysis and calculations employed in many embodiments of the present invention. Tissue response and healing effects may be influenced by biometric co-factors, such as the patient's age, gender, race, and/or the like. Specific identification of the measurement and/or treatment system components may be included among the co-factors by identification of a treatment laser system model, a diagnostic system type identifier, a specific diagnostic system identification, the identification of the diagnostic measurement and/or treatment physician, treatment and/or measurement ambient room temperatures and humidities, measurement or treatment times during the day, patient apprehension levels, and the like. Exemplary embodiments may still allow physicians to input adjustment factors and nomogram adjustments so as to alter the overall refractive prescription per a physician's experience. Advantageously, the ablation shot tissue removal basis and data used in calculating the shot numbers and locations so as to approximate an overall desired refractive prescription shape need not be altered to take advantage of the improvements provided by the inventions described herein. Additionally, the holistic vector function approach described herein is compatible with more specific analysis of factors which influence specific couplings between an intended change in the refractive properties of a patient's eye and the resultant high-order changes, so that analysis of the components of the influence function (or other matrix analysis components) can be performed and values may even be prophetically revised to reflect new changes in the overall diagnostic and/or treatment components.

FIG. 1 schematically illustrates a simplified system 0 according to an embodiment of the invention. System 0 includes a measurement device 1 used during a diagnostic procedure and a laser surgery system 5 used during a treatment procedure. The diagnostic procedure for a particular eye may precede the treatment the procedure on that eye by minutes, hours, days, or weeks. A timed series of diagnostic measurements may be taken, with times between measurements optionally being quite short, though in some cases being several days or weeks apart so that stability of the measurements can be checked. Measurements will also often be acquired after the treatment is complete, with at least some of the measurements ideally being acquired a significant time after treatment so as to allow healing and any other tissue responses to the treatment to fully progress and for the treated eye to return to a substantially stabilized refractive system.

Exemplary measurement system 1 includes a wavefront measurement device 2 such as a Hartmann-Shack wavefront aberrometer. An imaging assembly 25 is also included to capture an image of the eye at substantially the same time (so that the eye does not move between the image and the measurement) that wavefront measurement device 2 directs a beam 3 toward the eye 15 of a patient in a diagnostic procedure. Directing of the laser beam 3, acquisition of the measurement data, capturing of the image, and other measurement parameters are under the direction of an overall computer system 35 of the system 0. As the wavefront measurement and image are substantially contemporaneous, and as the structures of the imaging assembly in the measurement device are optically and/or mechanically coupled, the location information included in the image and the measurement can be associated.

In some embodiments, the computer system 35 of the image capture device 1 may also generate and save additional treatment information, such as a planned ablation profile or desired laser resculpting. Such treatment information can be generated from the data acquired by wavefront measurement device 2, and may be downloaded from diagnostic system 1 to a processor 22 of laser treatment device 5. Suitable measurement systems may include structures such as (or based on) the WaveScan Wavefront® system commercial available from Abbott Medical Optics, Inc. (AMO) of Santa Ana, Calif.; the Zyoptix® diagnostic workstation commercial available from Bosch and Lomb of Rochester, N.Y., and others. Exemplary diagnostic systems may include integrated wavefront and topographic systems such as those being developed for commercial and clinical use by TopCon Corporation of Japan, such as the iDesign™ integrated eye measurement system being developed by Abbott Medical Optics of California, and the like. Hence, along with overall measurement of the aberrations throughout the optical system of the eye, the aberration data may more specifically identify the source of the aberrations, such as through topographic measurements of the anterior surface of the cornea, measurements of the posterior surface of the cornea (via optical coherence tomography, OCT) measurements of the size, shape, and aberrations of the crystalline lens, and the like.

The laser system 5 includes a laser 55 such as an excimer laser, a femtosecond laser, or the like. An imaging assembly 6 obtains an image of the eye, and as the images can be acquired substantially contemporaneously with refractive treatment of the eye using laser 55, registration of the treatment images from imaging assembly 6 and diagnostic images from imaging assembly 25 allow the therapeutic laser beam 65 to be accurately directed to eye 15. Registration of the images and directing of the laser beam are performed by processor 22. In the exemplary embodiment, processor 22 directs pulses of excimer laser energy toward stromal tissue of the cornea so as to effect volumetric reshaping of the cornea. Alternative refractive laser systems may employ femtosecond pulses to form an incision, and in some embodiments, separate lasers may be employed to first cut a flap in the cornea to expose the stroma underlying the epithelial tissue, and thereafter volumetrically resculpt the exposed stroma so as to alter the refractive characteristics of eye 15. In some embodiments, the ablation profile generated by other components of processor 22 for calculation of a desired refractive correction in the components of treatment system 5. Hence, the overall computer system of the combined devices may generally be referred to as a single computer system 35, of which processor 22 is a component. Specific processing tasks may be performed by any of a wide variety of processors, and/or by software organized into a wide variety of subroutines.

Figure 1A:
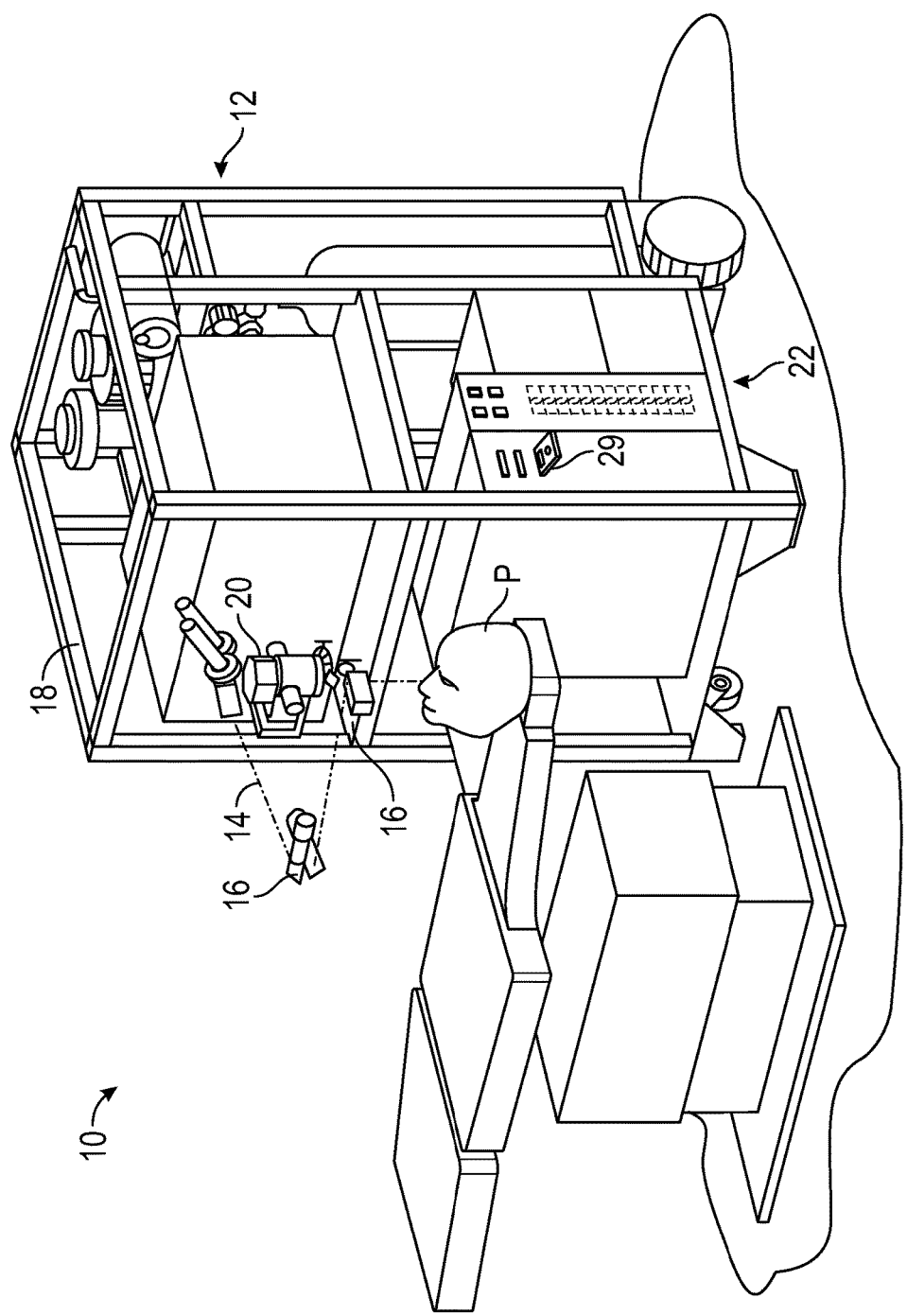
FIG. 1A is a perspective view schematically illustrating a refractive treatment of an eye of a patient using a laser eye surgery system, as may be included in the system of FIG. 1.

Referring now to FIG. 1A, a laser eye surgery system 10 may be employed as treatment system 5 in the schematic of FIG. 1. Laser eye surgery system 10 includes a laser 12 that produces a laser beam 14. Laser 12 is optically coupled to a laser delivery optic system 16, which directs laser beam 14 to an eye of patient P. The delivery optics support structure (not shown here for clarity) extends from a frame 18 supporting laser 12. A microscope 20 is mounted on the delivery optics support structure, the microscope often being used to image the cornea of the eye.

Processor 22 of laser system 10 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may also optionally embody wavefront sensor data, wavefront gradients, a wavefront elevation map, a treatment map, a corneal elevation map, and/or an ablation table. While tangible storage media 9, will often by used directly in cooperation with an input device of processor 22, the storage media may also be remotely operatively coupled with processor by means of network connections such as the internet, and by wireless methods such as infrared, Bluetooth, or the like. Many other hardware system architectures could also be implemented.

Laser 12 and delivery optics 16 will generally direct laser beam 14 to the eye of patient P under the direction of processor 22. Processor 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table.

Laser beam 14 may be adjusted to produce the desired sculpting using a variety of alternative mechanisms. The laser beam 14 may be selectively limited using one or more variable apertures. The laser beam may also be tailored by varying the size and offset of the laser spot from an axis of the eye. Still further alternatives are possible, including scanning of the laser beam over the surface of the eye and controlling the number of pulses and/or dwell time at each location; using masks in the optical path of laser beam 14 which ablate to vary the profile of the beam incident on the cornea; hybrid profile-scanning systems in which a variable size beam (typically controlled by a variable width slit and/or variable diameter iris diaphragm) is scanned across the cornea; or the like. The optical and electromechanical computer programs, hardware, and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam. Optional ablation effluent evacuators/filters, aspirators, and other ancillary components of the laser surgery system are known in the art. Suitable systems may also include commercially available refractive laser systems manufactured and/or sold by Abbott Medical Optics, Alcon, Bausch & Lomb, Nidek, WaveLight, LaserSight, Schwind, Zeiss-Meditec, and the like.

Figure 2:
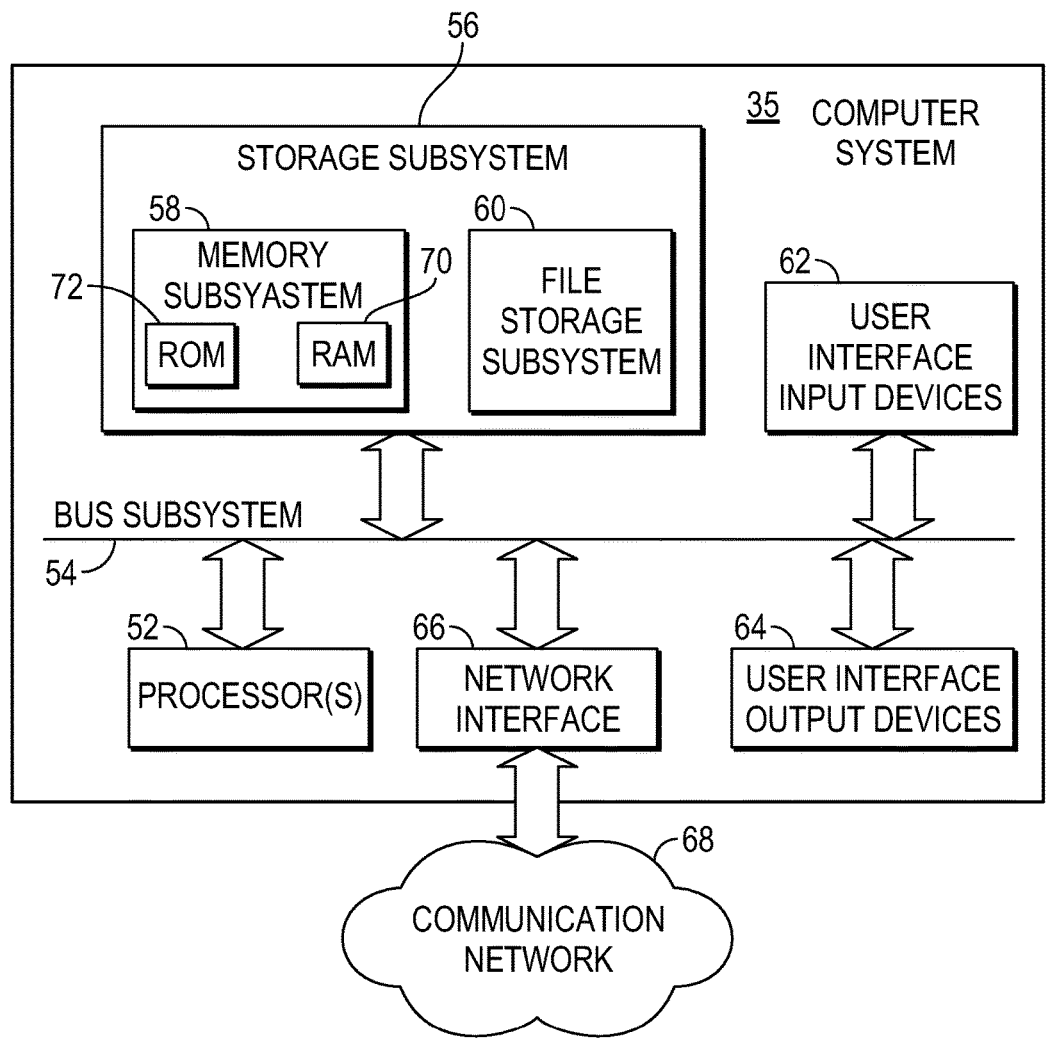
FIG. 2 schematically illustrates components of a simplified computer system for use in the diagnostic and/or treatment components of the system of FIG. 1.

FIG. 2 is a simplified block diagram of exemplary overall computer system 35 that may be used by the system 0 (see FIGS. 1 and 1A) of the present invention. Computer system 35 typically includes at least one processor 52 (and, optionally, processor 22) which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 35.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 35 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52, and/or by processor 22 (see FIGS. 1 and 1A). In a distributed environment, the software modules may be separated and stored on a plurality of computer systems 22, 35 and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1A) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 35. The modules implementing the functionality of the present invention may be stored by file storage subsystem 60.

Bus subsystem 54 provides a mechanism for letting the various components and subsystems of computer system 35 communicate with each other as intended. The various subsystems and components of computer system 35 need not be at the same physical location but may be distributed at various locations within a distributed network. Although bus subsystem 54 is shown schematically as a single bus, alternate embodiments of the bus subsystem may utilize multiple busses.

Computer system 35 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 35 depicted in FIG. 2 is intended only as an example for purposes of illustrating one embodiment of the present invention. Many other configurations of computer system 35 are possible having more or less components than the computer system depicted in FIG. 2.

Figure 3:
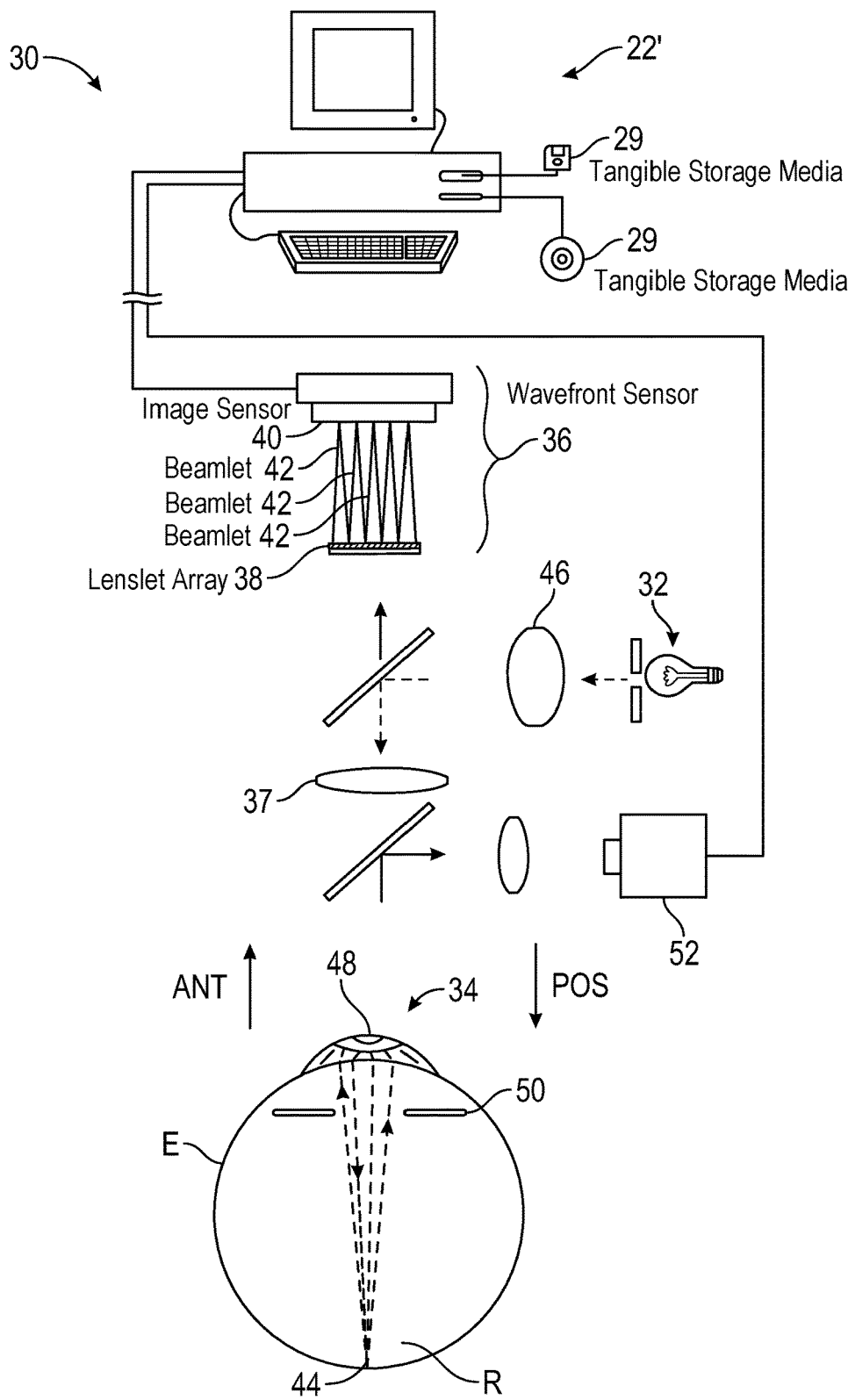
FIGS. 3 and 4 illustrate other wavefront measurement systems for use in the system of FIG. 1.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a process 22' for measurement of the optical errors in the optical tissues 34 and/or determination of an optical tissue ablation treatment program. Process 22' may be incorporated in the overall computer system 35, and may optionally make use of the same or similar hardware as the processor 22 and/or 52 illustrated in FIGS. 1, 1A and 2. Processor 22' may be in communication with processor 22 that directs the laser surgery system 10, or some or all of the components of computer system 35 of the wavefront measurement system 30 and laser surgery system 10 may be combined or separate. If desired, data from wavefront sensor 36 may be transmitted to a laser processor 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beam lets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information may be sufficient to reconstruct the wavefront or any desired portion of it. The data space to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target. By varying a position of the fixation target as described in that reference, optical characteristics of the eye may be determined while the eye accommodates or adapts to image a field of view at a varying distance.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 4:
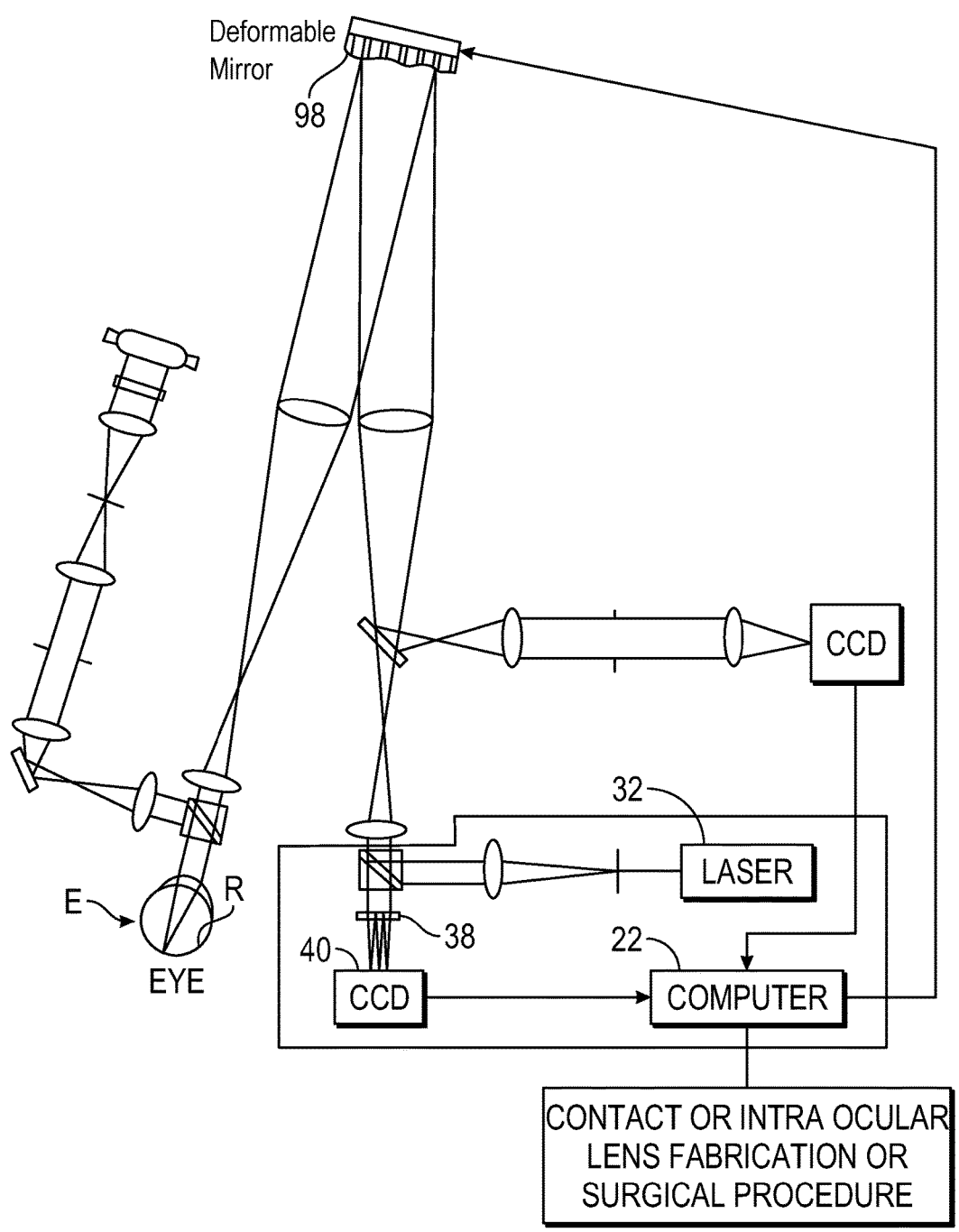

An alternative embodiment of a wavefront measurement system is illustrated in FIG. 4. The major components of the system of FIG. 4 are similar to those of FIG. 3. Additionally, FIG. 4 includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by processor 22 to limit distortion of the image formed on the retina or of subsequent images formed of the images formed on the retina, and may enhance the accuracy of the resultant wavefront data. The structure and use of the system of FIG. 4 are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from ABBOTT MEDICAL OPTICS of California. It is appreciated that other wavefront aberrometers could be employed with the present invention. Relatedly, embodiments of the present invention encompass the implementation of any of a variety of optical instruments provided by WaveFront Sciences, Inc., including the COAS wavefront aberrometer, the Clear-Wave contact lens aberrometer, the Crystal Wave IOL aberrometer, the iDesign eye measurements system, and the like.

Figure 5A:
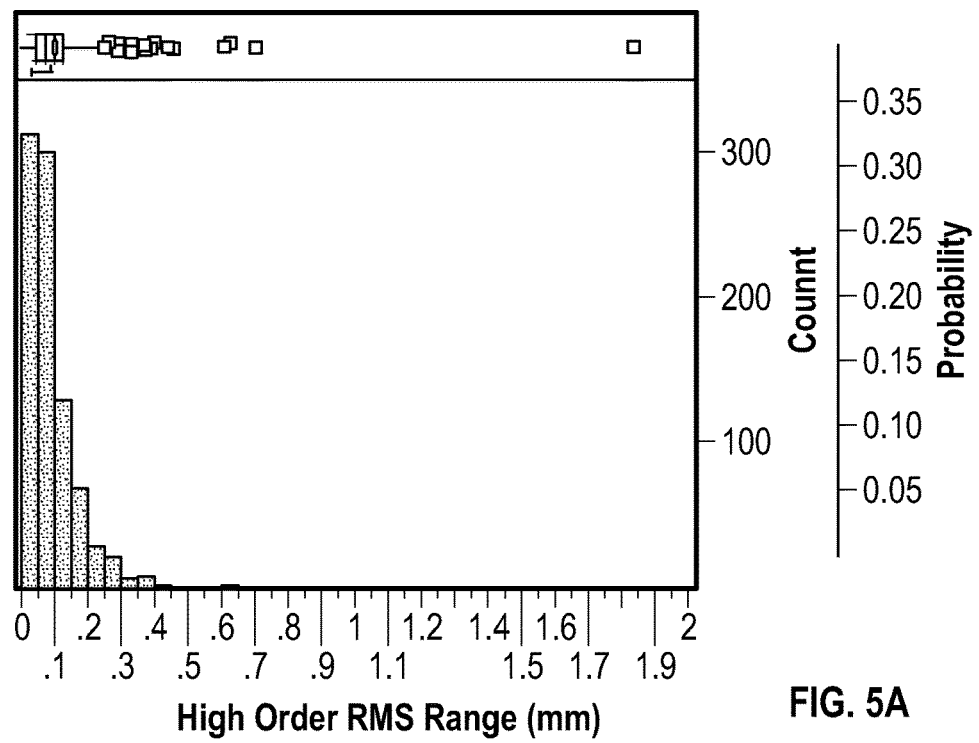
FIGS. 5A and 5B graphically illustrate a statistical range of pre-treatment high-order aberration (HOA) measurements, showing an accuracy of these measurements.
Figure 5B:
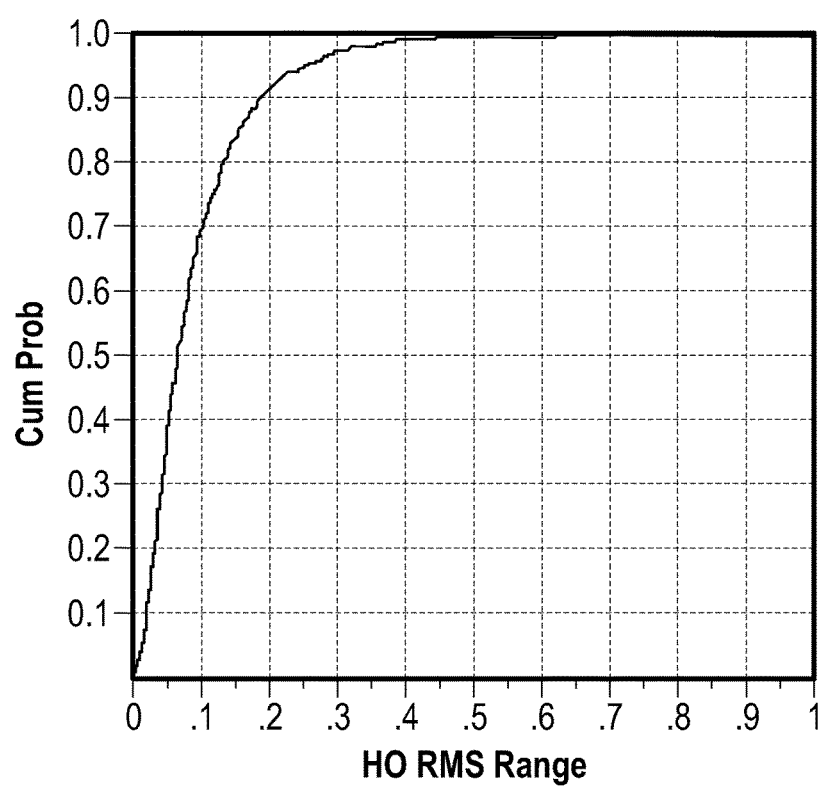

Referring now to FIGS. 5A and 5B, known laser eye surgical system treatments have not always been as effective at reducing or eliminating high-order optical aberrations of the eye as has been expected. The accuracy with which high-order optical aberrations can be measured may ultimately determine the precision with which treatment plans may be derived. Fortunately, known wavefront aberration systems are capable of measurement of the human eye with quite good accuracy. FIG. 5A shows a count and probability plot (along the vertical axis) for differing high-order root mean square (RMS) ranges for pre-treatment measurements of eyes in a series of studies. The mean range of pre-treatment measurements was about 93 microns. As illustrated by the cumulative distribution function plot of FIG. 5B, this relatively low measurement error was fairly consistent throughout the several hundred eyes of the studies. Hence, if overall treatment accuracy were limited solely by measurement accuracy, treatment should be very effective at decreasing or eliminating high-order aberrations.

To more fully analyze the interaction between eye measurements, planned treatments, the treatment that is actually performed on the eye, and the subsequent effects of healing (including epithelial regrowth, recovering from fluid-induced swelling or hydration effects, and the like), it is beneficial to measure a total effective treatment that has been rendered to an eye. The effective treatment may be defined as follows:

Treatment=Post Op−Pre Op in which Treatment here refers to a vector characterizing an effective treatment or change in refractive properties (including high-order aberrations), in which "Post Op" refers to a high-order vector characterization (typically including a wavefront measurement) after the refractive treatment to an eye and after the eye has been allowed to stabilize, and in which "Pre Op" refers to a high-order vector characterization (typically including a measurement of the wavefront) before refractive treatment of the eye.

Ideally, the Treatment should not correlate to the Pre Op measurement, as there will ideally be zero Post Op aberration. Unfortunately, known laser eye surgery measurement and treatment systems have not uniformly provided this ideal outcome.

Figure 6A:
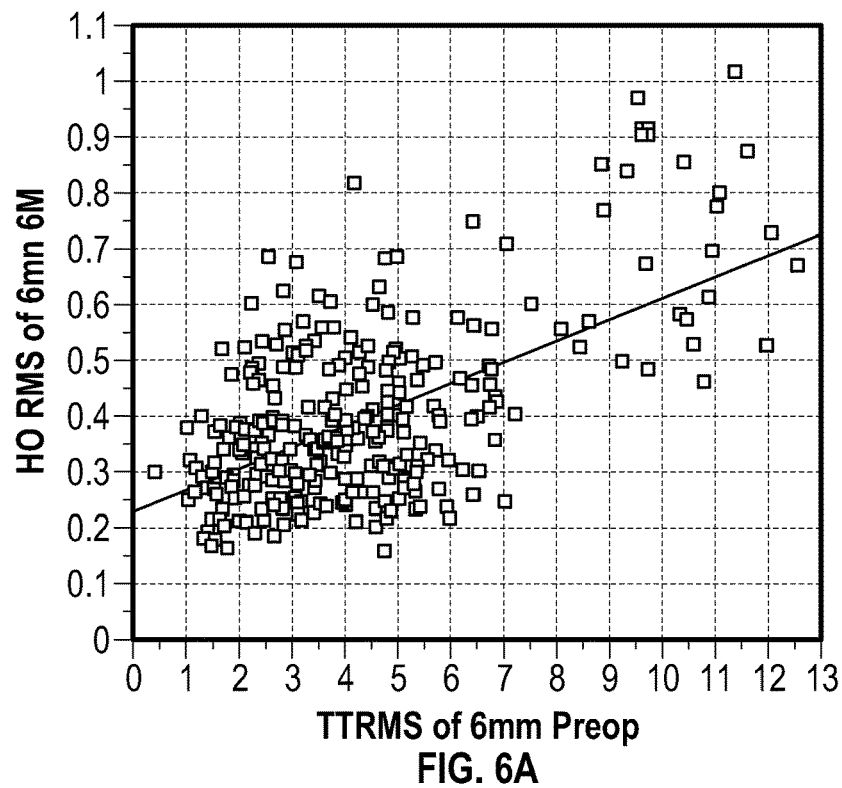
FIG. 6A illustrates a data plot of post-treatment high-order aberrations versus total pre-treatment aberrations.

Referring now to FIG. 6A, a plot of post-treatment high-order optical aberrations (along the vertical axis) against total measured pre-treatment aberrations (along the horizontal axis) for each of a plurality of previously treated eyes shows a significant correlation. Since the total aberration is dominated by the standard low-order refraction terms, there appears to be a significant undesirable coupling between the refraction or low-order aberration terms of eyes before treatment and high-order aberrations of the eyes after treatment. Note that the data FIG. 6A shows data from eyes that were measured before treatment using wavefront measurement systems such as those described above. The eyes were then treated using refractive laser eye surgery systems, with customized refractions being derived for each eye based on the measured aberrations (including both standard refractive errors and high-order aberrations) for that eye. Post-treatment measurements of the eye were performed a significant amount of time (such as 6 months) after the treatments so that healing is largely completed and the refractive properties of the eye have substantially stabilized.

Figure 6B:
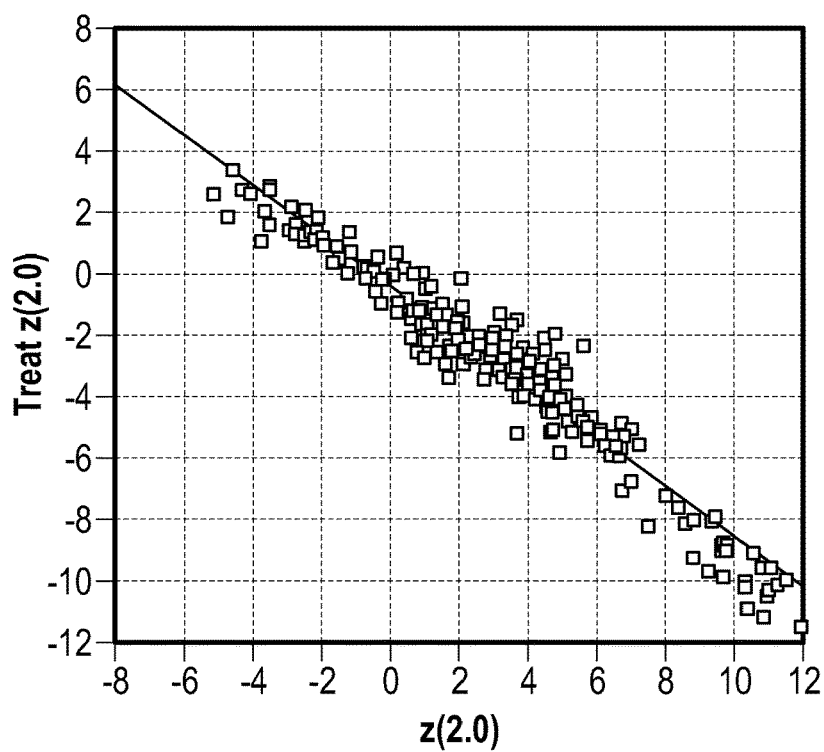
FIG. 6B is a data plot showing a strong correlation between an effective spherical defocus treatment and a pre-treatment measured spherical defocus, indicating effective treatment of low-order errors.

Referring now to FIG. 6B, existing laser eye surgery systems do a quite good job at correcting standard refractive errors. Individual components of the eye aberrations may be referenced using their standard Zernike coefficient numbers, as seen in the table below. The defocus term Z (2,0) of the effective treatment is plotted along the vertical axis, and the same coefficient for the Pre Op eye is plotted along the horizontal axis. A slope near −1 indicates that for each unit of defocus of the eye before treatment, the effective treatment substantially removed that same amount of error from the eye. Hence per this data, existing laser eye surgical systems (including their associated measurement systems) can do a good job in correcting standard refractive errors of the eye.

TABLE

| j = index | n = order | m = frequency | $Z_n^m (\rho, \theta)$ |
|---|---|---|---|
| 0 | 0 | 0 | 1 |
| 1 | 1 | −1 | $2 \rho \sin \theta$ |
| 2 | 1 | 1 | $2 \rho \cos \theta$ |
| 3 | 2 | −2 | $\sqrt{6} \rho^2 \sin 2\theta$ |
| 4 | 2 | 0 | $\sqrt{3} (2\rho^2 - 1)$ |
| 5 | 2 | 2 | $\sqrt{6} \rho^2 \cos 2\theta$ |
| 6 | 3 | −3 | $\sqrt{8} \rho^3 \sin 3\theta$ |
| 7 | 3 | −1 | $\sqrt{8} (3\rho^3 - 2\rho) \sin \theta$ |
| 8 | 3 | 1 | $\sqrt{8} (3\rho^3 - 2\rho) \cos \theta$ |
| 9 | 3 | 3 | $\sqrt{8} \rho^3 \cos 3\theta$ |
| 10 | 4 | −4 | $\sqrt{10} \rho^4 \sin 4\theta$ |
| 11 | 4 | −2 | $\sqrt{10} (4\rho^4 - 3\rho^2) \sin 2\theta$ |
| 12 | 4 | 0 | $\sqrt{5} (6\rho^4 - 6\rho^2 + 1)$ |
| 13 | 4 | 2 | $\sqrt{10} (4\rho^4 - 3\rho^2) \cos 2\theta$ |
| 14 | 4 | 4 | $\sqrt{10} \rho^4 \cos 4\theta$ |
| 15 | 5 | −5 | $\sqrt{12} \rho^5 \sin 5\theta$ |
| 16 | 5 | −3 | $\sqrt{12} (5\rho^5 - 4\rho^3) \sin 3\theta$ |
| 17 | 5 | −1 | $\sqrt{12} (10\rho^5 - 12\rho^3 + 3\rho) \sin \theta$ |
| 18 | 5 | 1 | $\sqrt{12} (10\rho^5 - 12\rho^3 + 3\rho) \cos \theta$ |
| 19 | 5 | 3 | $\sqrt{12} (5\rho^5 - 4\rho^3) \cos 3\theta$ |
| 20 | 5 | 5 | $\sqrt{12} \rho^5 \cos 5\theta$ |
| 21 | 6 | −6 | $\sqrt{14} \rho^6 \sin 6\theta$ |
| 22 | 6 | −4 | $\sqrt{14} (6\rho^6 - 5\rho^4) \sin 4\theta$ |
| 23 | 6 | −2 | $\sqrt{14} (15\rho^6 - 20\rho^4 + 6\rho^2) \sin 2\theta$ |
| 24 | 6 | 0 | $\sqrt{7} (20\rho^6 - 30\rho^4 + 12\rho^2 - 1)$ |
| 25 | 6 | 2 | $\sqrt{14} (15\rho^6 - 20\rho^4 + 6\rho^2) \cos 2\theta$ |
| 26 | 6 | 4 | $\sqrt{14} (6\rho^6 - 5\rho^4) \cos 4\theta$ |
| 27 | 6 | 6 | $\sqrt{14} \rho^6 \cos 6\theta$ |
| 28 | 7 | −7 | $4 \rho^7 \sin 7\theta$ |
| 29 | 7 | −5 | $4 (7\rho^7 - 6\rho^5) \sin 5\theta$ |
| 30 | 7 | −3 | $4 (21\rho^7 - 30\rho^5 + 10\rho^3) \sin 3\theta$ |
| 31 | 7 | −1 | $4 (35\rho^7 - 60\rho^5 + 30\rho^3 - 4\rho) \sin \theta$ |
| 32 | 7 | 1 | $4 (35\rho^7 - 60\rho^5 + 30\rho^3 - 4\rho) \cos \theta$ |
| 33 | 7 | 3 | $4 (21\rho^7 - 30\rho^5 + 10\rho^3) \cos 3\theta$ |
| 34 | 7 | 5 | $4 (7\rho^7 - 6\rho^5) \cos 5\theta$ |
| 35 | 7 | 7 | $4 \rho^7 \cos 7\theta$ |

Figure 7A:
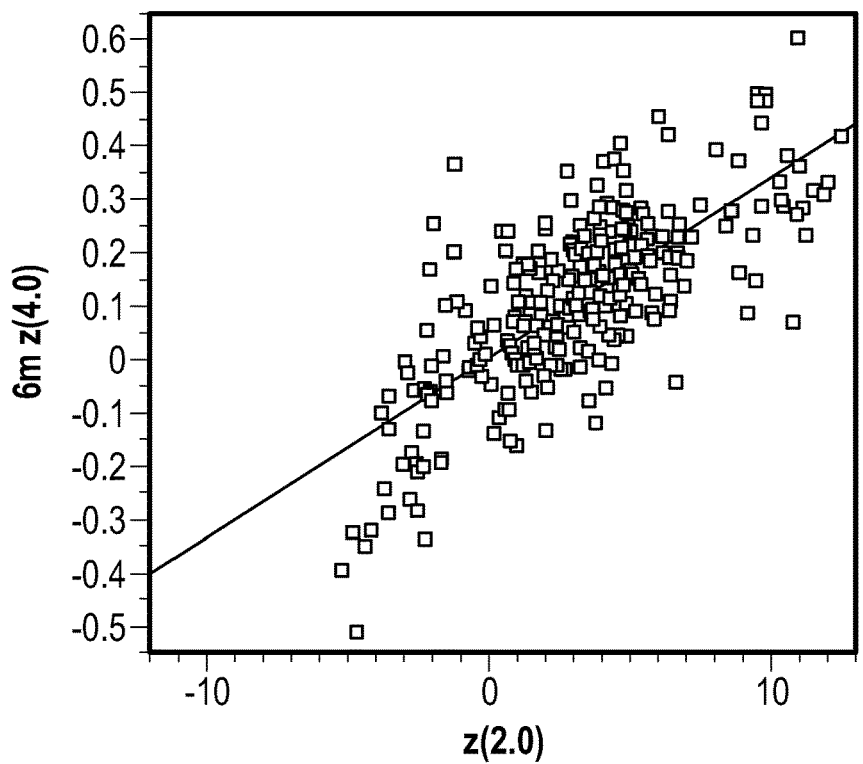
FIGS. 7A and 7B illustrate data plots analogous to FIG. 6B, but showing correlations between pre-treatment aberrations and post-treatment high-order aberrations that indicate potential inducement of some high-order aberrations.
Figure 7B:
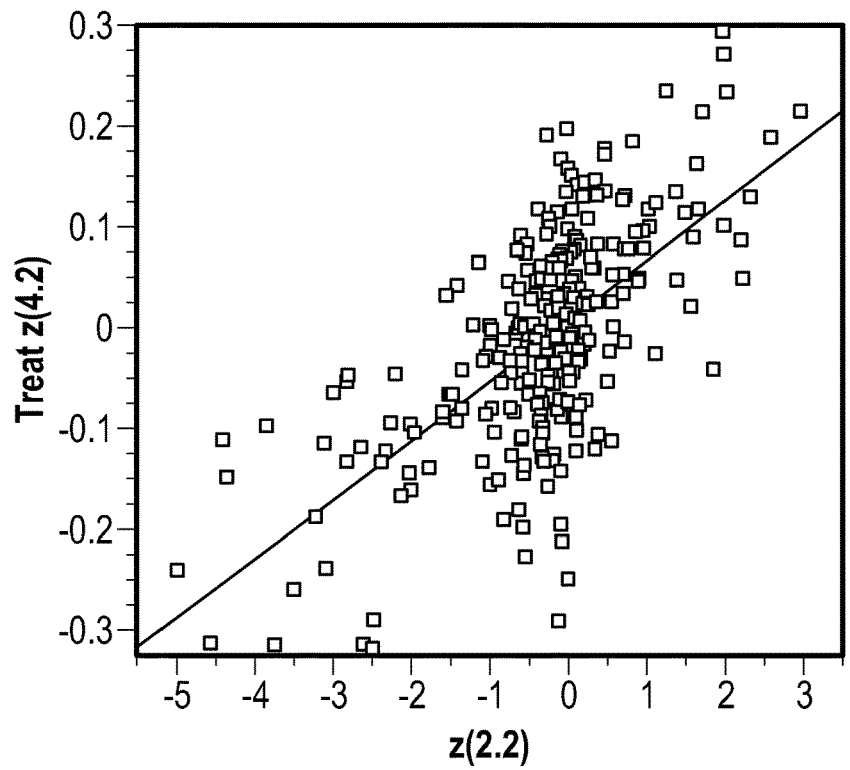

Referring to FIGS. 7A and 7B, the total response of the eyes to the measurement and treatment may be more complex when individual high-order aberrations are analyzed. For example, as illustrated in FIG. 7A, a measured Post Op aberration in the Z (4,0) term (plotted on the vertical axis) has a positive correlation relative to measured pre-treatment defocus on Z (2,0) (plotted o the horizontal axis). In other words, the positive slope of the graph of FIG. 7A indicates the Z (4,0) high-order spherical aberration term may be induced in proportion to the amount of defocus that is being corrected. This discrete relationship may optionally be used to develop a specific adjustment or nomogram for future eyes, thereby seeking to avoid inducing such errors. Unfortunately, the total number of such correlations between high-order aberrations are sufficiently complex that seeking to adjust the treatments using such discrete nomograms for each identified correlation may be both challenging and, in the end, less than ideally effective. For example, as illustrated in FIG. 7B, a significant pre-treatment error in the Z (2,2) high-order aberration term may be coupled to a significant treatment Z (4,2) term. Given enough of these discrete correlations, a nomogram adjustment approach may end up resolving some errors while inducing others, particularly where knowledge regarding all of the discrete couplings is less than perfect.

Figure 8A:
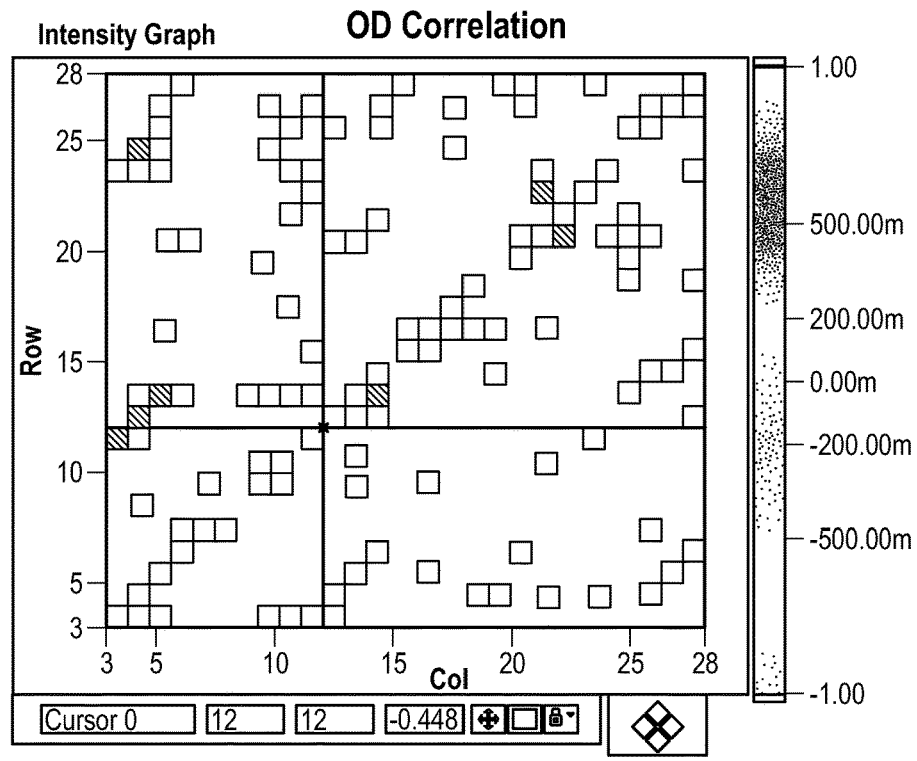
FIGS. 8A and 8B graphically illustrate correlations between effective treatment high-order aberrations and measured pre-treatment high-order aberrations for the right eye and left eye, respectively.
Figure 8B:
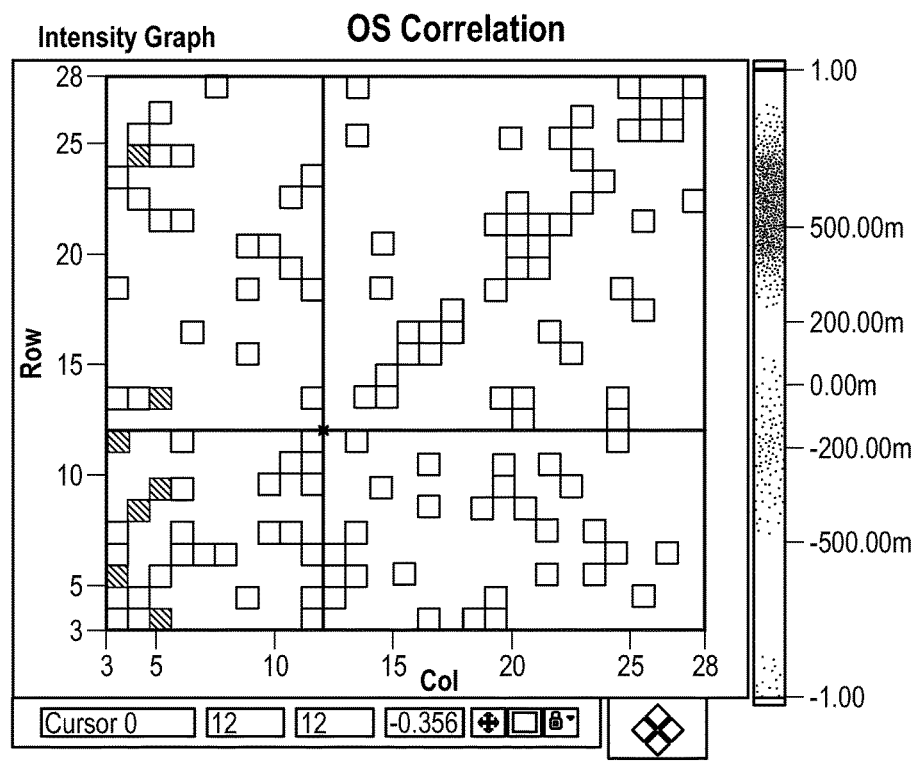
Figure 8C:
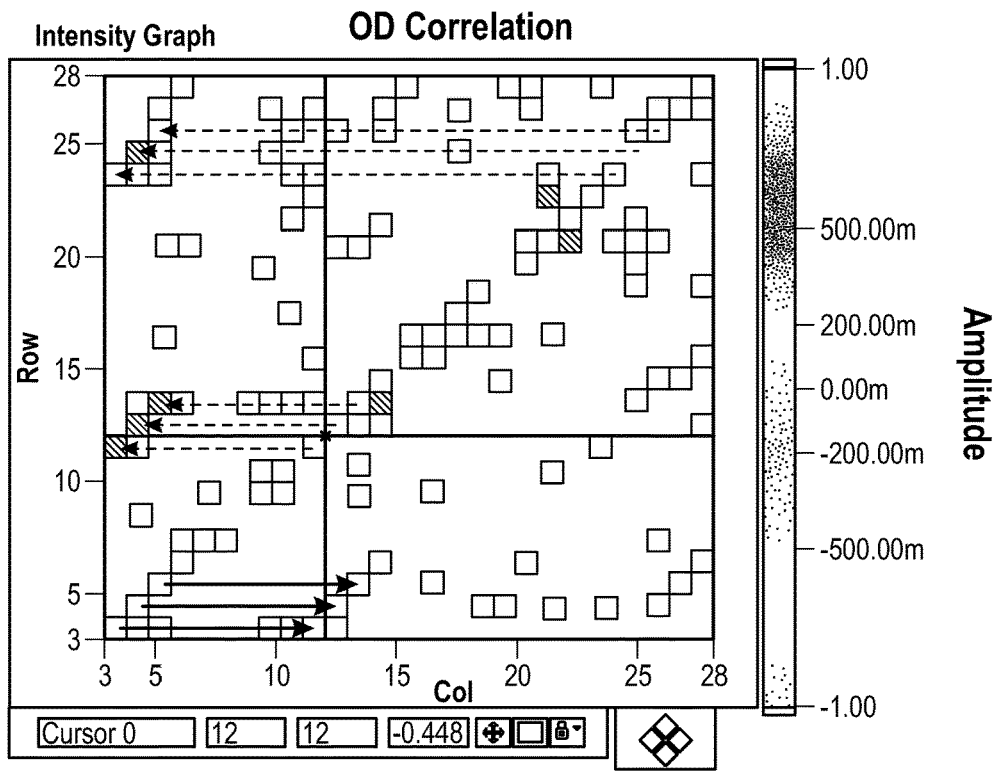
FIG. 8C identifies a few selected exemplary couplings between induced high-order aberrations and pre-treatment measured high-order aberrations.

Referring now to FIGS. 8A and B, a graphical representation of a correlation matrix between the treatment and pre-op wavefront measurements indicates the large number and intensities of correlations between differing Zernike globally Zernike—Zernike terms. Each axis number illustrated in FIGS. 8A and 8B corresponds to a specific Zernike coefficient, starting with Z(-2,2) (Zernike #3) through Z(6, 6). If planned treatments altered the target aberrations in the amounts desired (and imposed no other induced aberrations, i.e., had no couplings to other aberration modes), the values along the diagonal extending from 3,3 to 28,28 would all be negative 1, and all values other than those along the diagonal would be 0. As indicated in FIGS. 8A and 8C, existing diagnostic and treatment systems do not provide this idealized result. Instead, there are significant correlations for many of the Zernike terms between the effective treatment and the pre-treatment aberration measurements off the diagonal.

The correlations between pre-operative measurements and effective treatment coefficients are relatively high for the refractive term numbers 3 through 5. Unfortunately, many of the diagonal elements are significantly different than the ideal 1 value, and many of the off-diagonal elements are significantly different than the ideal 0 value. Note that differences in sign and values of the correlations may be associated with the different eyes, with the right eye having significantly different values then the left eye. For example, horizontal aberration terms for Zernike 7 and 8 are different.

Referring now to FIG. 8C, selected terms have been highlighted with relatively low angular or even radial coefficients. Specifically, pre-operative measurement identifying defocus (Zernike #4) induces spherical aberration (Zernike #12) in the treatment, as indicated by the sign of the correlation. Similarly, second order astigmatism is induced in the effective treatment when correcting for measured pre-operative astigmatism. Some crossover coupling between the astigmatism terms is also evident (between Zernike #3 and Zernike #5) within the second radial order. These may be among the most significant terms of the couplings matrix, because the refraction terms are generally the far largest measured pre-operative aberrations in an eye. Nonetheless, most or even all other off-diagonal elements will contribute to aberrations (in other words, inducing at least some aberrations after treatment) at some (typically lesser) level. Some of the more important couplings identified in the correlation matrix are graphically illustrated in FIG. 9.

Figure 10:
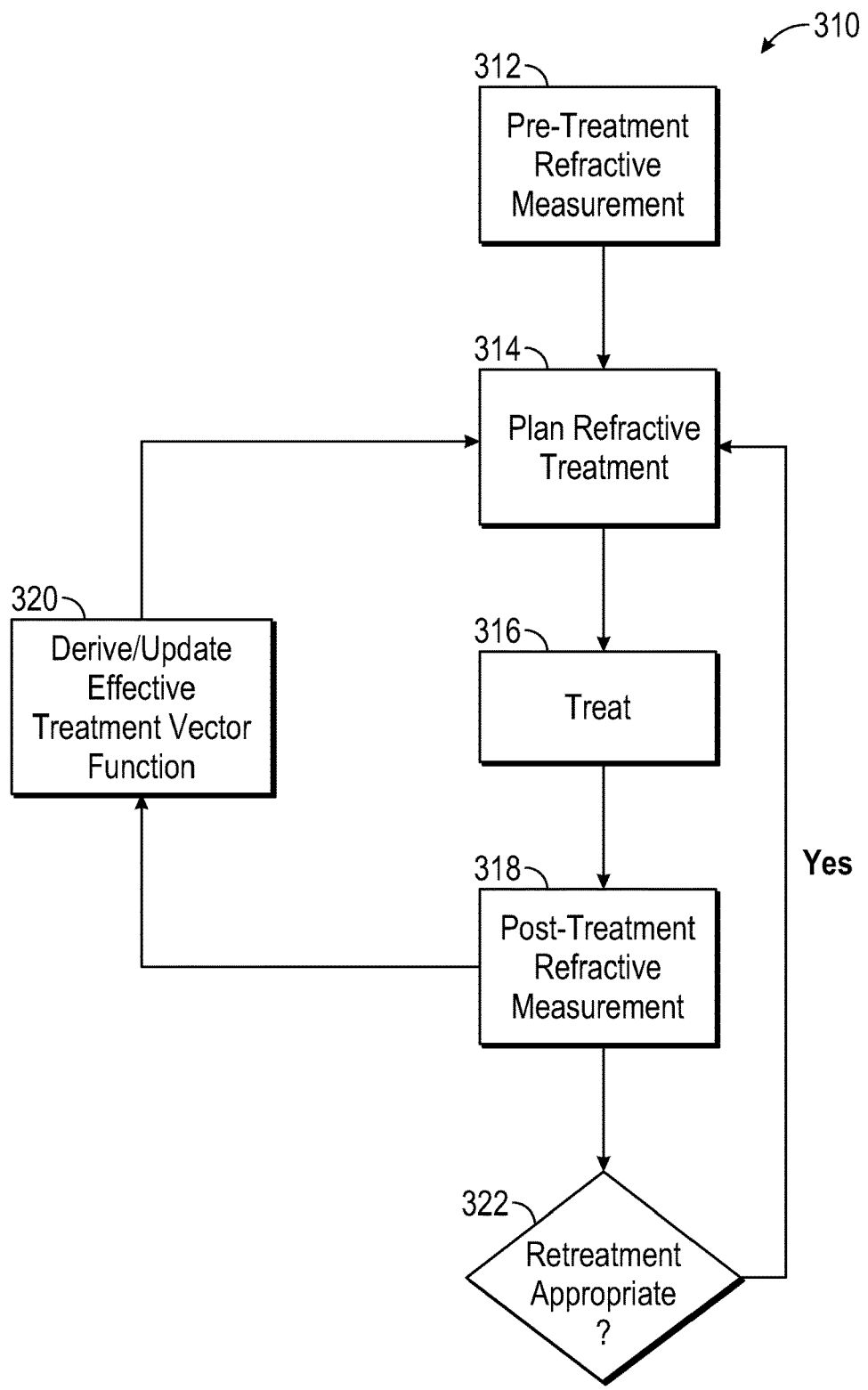
FIGS. 10 and 10A are functional block diagrams schematically illustrating processing components and methods for eye treatments, including relationships between measurement and treatment parameters.

Referring now to FIG. 10, an overview of an improved treatment and treatment improvement methodology 310 begins for a particular patient with a pre-treatment refractive measurement 312. A refractive treatment plan is developed 314, and the patient is treated 316 so as to correct refractive defects identified in the measurement 312. After treatment, a post-treatment refractive measurement of the treated eye is taken 318.

Post-treatment measurement 318 has at least 2 distinct advantages. First, it verifies that the intended refractive change has been imposed on the patient's eye, thereby giving information regarding that specific patient. In addition, the post-treatment measurement 318 provides feedback information which can be used for development of refractive treatment plans 314 for treatment of other eyes in the future. In exemplary embodiments of the methods described herein, the feedback from prior treatments is affected by deriving and/or updating an effective treatment vector function 320.

Regarding the use of post-treatment measurements 318 for the treated patient, these measurements may provide an indication whether retreatment is appropriate 322. For example, if the post-treatment measurement differs from an expected characterization of the eye by more than a threshold amount, retreatment of the eye (such as a new repeated LASIK treatment or the like) may be planned 314 and then implemented 316. Target refractive measurements and associated variation thresholds may be established for one or more specific time intervals after treatment 316. For example, an immediate post-treatment refractive measurement 318 on the day of treatment 316 may have one expected set of refractive properties and range of acceptable variations, while a two-week or six-month follow up post-treatment refractive measurement 318 may each have differing values. Hence, post-treatment measurement 318 may comprise a series of measurements. The retreatment decision 322 may also occur repeatedly over the days, weeks, months, or even years after treatment 316.

Figure 9:
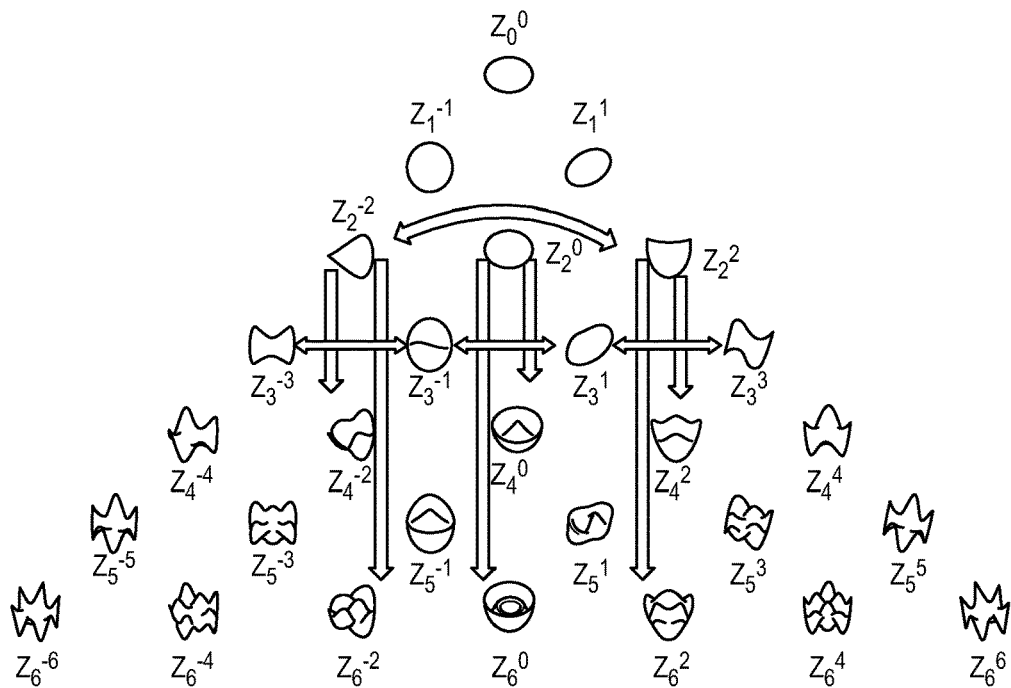
FIG. 9 schematically illustrates selected couplings.

More detailed understanding of the information displayed in FIGS. 8A through 9 can be obtained through defining and more rigorously analyzing some of the terms. A Surgically-Induced Refractive Correction (SIRC) may be defined as the actual change in measured wavefront induced by the surgery. The vector SIRC may thus be defined mathematically as follows:

$$SIRC = Post\ Op - Pre\ Op$$

The vector elements may here include a described number of Zernike coefficients. Another vector, the Intended Refractive Correction (IRC) is the change in refractive properties that is the goal of the treatment. When the intended outcome of the treatment is an emmetropic eye, we may calculate IRC as being effectively equal to the negative of the pre-treatment aberration measurement Pre Op vector as follows:

$$IRC = Pre\ Op$$

Note that emmetropia is not necessarily the goal of many treatments. For example, it may be desirable to leave (or even induce) a small amount of myopia in one eye of a patient while the other eye is rendered emmetropic so as to provide sufficient monovision for mitigation of presbyopia. Alternatively, a variety of multifocal or aspherical presbyopic shapes may be desirable in the eyes of patients who have or will lose some or all of their ability to accommodate. When emmetropia is not the goal, we can calculate the IRC vector based on the measured pre-treatment aberrations and a vector characterizing the final resultant desired shape of the eye, Target, as follows:

$$IRC = Pre\ Op + Target$$

To provide the desired outcomes, it is beneficial for SIRC to approach or be equal to IRC, within physical optic limitations and clinical tolerances.

Applying our vector definitions to the overall treatment plan 310, pre-treatment refractive measurement 312 will generally result in definition of a Pre Op vector characterizing high-order aberrations of a particular patient's eye prior to receiving any treatment. Planning of the refractive treatment 314 defines the IRC intended refractive correction vector, with the IRC reflecting the Target vector when emmetropia is not the goal. Alternatively, when emmetropia is the goal, the target can be defined as an emmetropic target vector.

After treatment 316, post-treatment refractive measurements 318 provide, for each previously treated eye, a Post Op vector characterizing high-order aberrations of the eye. For each prior treatment, a surgically induced refractive correction SIRC can be defined as the difference between the Post Op vector and the Pre Op vector for that associated eye. The set of SIRC vectors can then be used to derive an effective treatment vector function 320. Where the effective treatment vector function 320 has previously been defined, new eye treatments (and their associated pre- and post-treatment measurements) can be used to update the effective treatment vector function. Hence, the effective treatment vector function 320 provides a feedback loop for planning refractive treatments 314 of new patients based on prior measurements and treatments of a number of eyes.

Figure 10A:
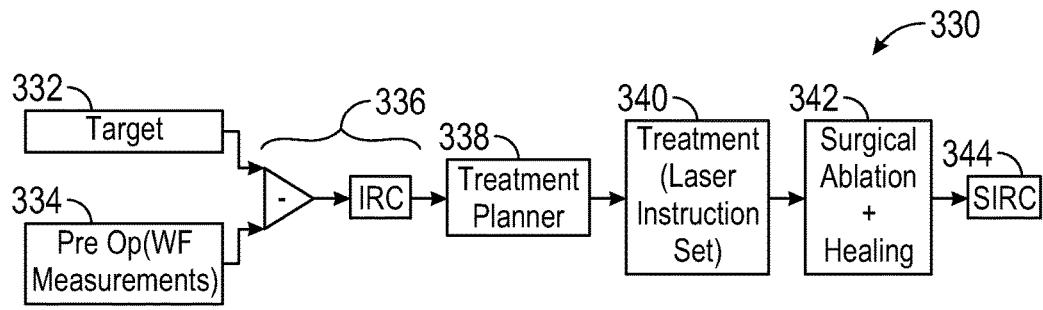

Referring now to FIG. 10A, a simplified block diagram schematically illustrates the input and output vector relationships for a particular patient, and also schematically provides a description of software modules associated with the vector elements described above. A target module 332 defines a Target vector or desired high-order characterization of the eye after treatment. Note that target module 332 may allow a physician and/or patient to select from a variety or range of target treatments. For example, a relatively young patient who seeks the best possible distance vision may desire emmetropia in both eyes, while patients of sufficient age to exhibit presbyopia may select a desired amount of myopia in one eye or an aspherical or multifocal refractive shape so as to provide a desired level of near vision for reading or the like. A Pre Op input module 334 accepts the wavefront or other measurements which characterize the high-order refractive properties of the eye. Hence, the Pre Op measurement input 334 will often be coupled to a wavefront aberrometer, topographer, and/or the like. An intended refractive correction IRC vector module 336 will calculate and store the intended refractive correction vector. Like the Target module 332 and Pre Op measurement module 334, IRC module 336 will typically be implemented via software and/or hardware of computer system 35 (see FIG. 1).

Continuing on with the simplified functional block diagram 330 of FIG. 10A, a treatment planning module 338 will derive a set of instructions corresponding to the Treatment vector for the refractive laser or other treatment structure to be used, and the Treatment instruction 340 will be stored for use. The Treatment instructions will typically include shot locations and numbers in a table, and the table will often be ordered so as to minimize thermal damage, expedite the speed of the procedure, and the like. Surgical ablation will be performed using a laser control module 342 (generally including many of the components described above regarding processor 22 of FIGS. 1 and 1A). The surgical ablation itself, along with post-treatment healing, will alter the final shape of the eye. Post-treatment measurements, together with the pre-treatment measurements can then be used to define the overall effective treatment SIRC in a surgically induced refractive correction treatment module 344.

Treatment planner 338 will often use basis data defining ablation depths for the target laser fluence(s) and spot size(s). This basis data will often have been measured on porcine and/or cadaver eyes, and use of this data may be tightly controlled by regulatory agencies such as the Food and Drug Administration. Note that the basis data need not exactly match ablation rates in in-vivo human eyes. For example, no healing may be included during measurement of the basis data. Nonetheless, the basis data can form an important foundation of regulatory approval for LASIK and other refractive correction procedures, particularly for previously approved refractive laser treatment systems. Advantageously, the basis data need not be altered so as to take advantage of the feedback methodology and systems improvements described herein.

An improved functional block diagram 350 and associated method include many of the components described above regarding FIG. 10A. However, rather than directly making use of the IRC vector, adjustments to the IRC are implemented so as to define an adjusted intended refractive correction vector AIRC for storage in an adjusted correction module 352.

A variety of discrete and/or systemic adjustments can be made to the IRC. For example, physicians using existing refractive laser treatment systems have experience at inputting physician adjustments into a physician adjustment module 354 based on their experiences, practices, and the like. Similarly, a number of nomogram adjustments are input 356 so as to alter treatments based on qualitative or quantitative factors for a specific patient. These inputs effectively close the loop between clinical outcomes and desired corrections to a particular patient's eye for certain aspects of the treatment, but do not necessarily comprehensively alter the treatment, particularly where couplings between alterations in one mode of high-order optical aberrations errors is intertwined with a number of potentially induced high-order optical aberrations in the treated eye. Still further adjustments to the IRC may also be incorporated, including adjusting of the planned treatment so as to compensate for reduced ablation depths at increasing angles of laser incidence upon the corneal tissue surface. The so-called cosine corrections and other adjustments (including chromatic adjustments) may be included in a chromatic and cosine correction module 358. Additionally, adjustments may be allowed based on still other factors. For example, measurements of manifest refraction or low-order aberrations may be input into a pre-treatment K input module 368.

Figure 10B:
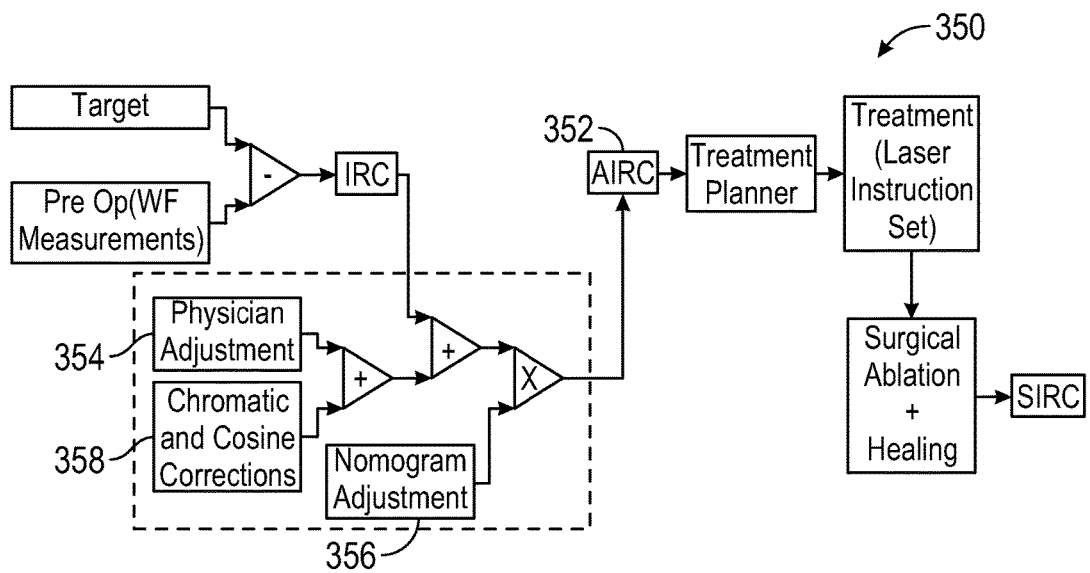
FIG. 10B is an improved functional block diagram schematically illustrating development of treatment plan parameters for improving clinical outcomes.
Figure 10C:
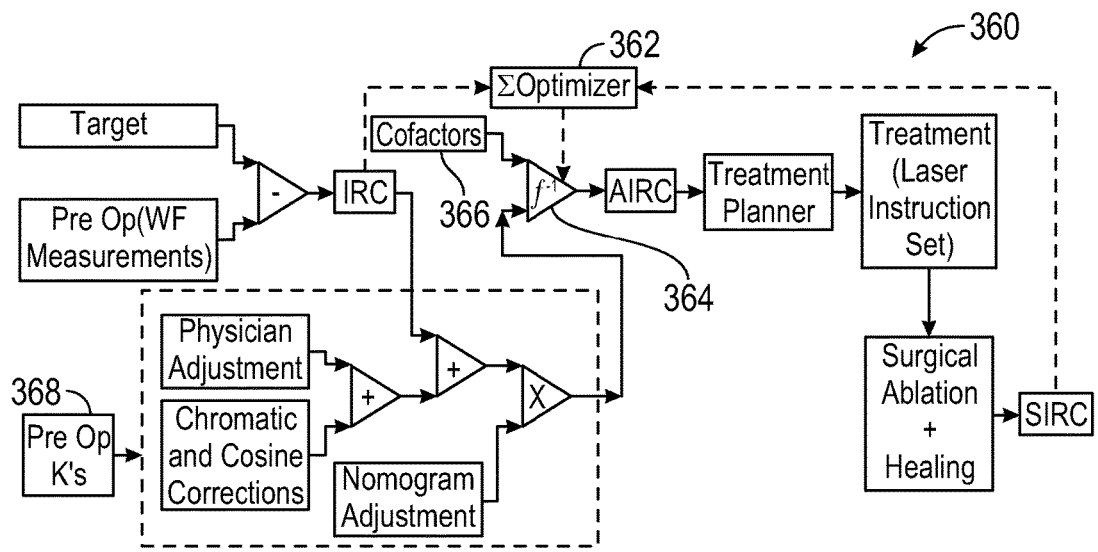
FIG. 10C is an improved functional block diagram illustrating an exemplary treatment plan solution to iteratively improve outcomes for successive patients by adjusting the treatment based on the effective treatments generated from prior treatments so as to mitigate induced high-order aberrations of the eye.

To more robustly make use of feedback from prior treatments, the functional block diagram 360 of FIG. 10C provides a more general solution that will improve outcomes, ideally via intermittent, regular, or continuous process improvements. Many of the method steps and associated modules are similar to those described above. However, the relationship between IRC and AIRC may be substantially more sophisticated. More specifically, rather than merely adjusting the low-order aberrations between the IRC and AIRC, the methodology of FIG. 10C will result in significant changes to the higher-order aberrations of the treatment to be performed. Improvements in the treatment may be performed by feeding back results of prior treatments via SIRC data from high-order aberration measurements into an effective treatment vector function deriving module 362 so as to generate an effective treatment vector function or adjustment function $f^{-1}$ 364. Note that the physician retains the ability to adjust treatments on an individual basis as described above regarding FIG. 10B. As generally described above, the effective treatment vector function $f^{-1}$ may also make use of co-factors (such as patient age, gender, race, measurement and/or treatment humidity, measurement and/or treatment physician identify, measurement and/or treatment system model number or identity, and the like). A co-factor module 366 may be used to input these co-factors into the processor module running the effective Treatment vector function 364.

Determination of the appropriate effective treatment vector function module 362 may optionally be described as an optimization. Note that the derivation of the appropriate function need not be an absolute optimization, but that the resulting vector function will preferably alter the IRC vector so as to result in significantly better vision after treatment and healing than would be provided without adjustment.

A number of mathematical approaches may be applied by module 362 to derive an appropriate adjustment vector function $f^{-1}$ and an associated function $f$. In the example below, a relatively simple linear algebra and multivarient regression approach are applied for deriving an influence matrix defining $f$. Note that more complex non-linear approaches could also be used.

As described above, the SIRC and IRC are expressed as vectors containing components with values that represent surgically-induced and intended refractive correction wavefront surfaces. SIRC vector also incorporates the Pre Op wavefront measurement surfaces prior to treatment in this exemplary embodiment. The vector elements may include Zernike coefficients that best describe the SIRC and IRC wavefront aberrations. The SIRC and IRC vectors may further contain keratometry values. Optional components of these vectors may include co-factor parameters that are known or suspected of influencing the SIRC, such as age, gender, humidity, water content of the cornea, and the like. The total number of components in each of these vectors may be designated as N.

It is generally desired to predict the SIRC produced by the system given an IRC. Toward this end, it can be assumed that the SIRC and IRC vectors are related through an influence matrix $f$ and an error vector E as follows:

$$\vec{E} = \overrightarrow{SIRC} - \overline{\overline{f}} \bullet \overrightarrow{IRC}$$

Advantageously, this mathematical model allows each component in the IRC to potentially contribute to every component in the SIRC, in the exemplary embodiment, in a linear fashion;

$$E_i = SIRC_i - \sum_j f_{ij} IRC_j$$

The components of $f$ may be identified or fit by taking clinical measurements of the SIRC and IRC optical aberration components as described above. Assuming there are m pairs of measurements of SIRC and IRC, each designated by the subscript k, a global merit function $\psi$ may be defined as follows:

$$\psi = \sum_{i,k} e_{ik}^2 = \sum_{i,k} \left( SIRC_{ik} - \sum_j f_{ij} IRC_{jk} \right)^2$$

In the merit function $\psi$, each unknown component of $f$ has an associated designation $f_{ij}$. We may minimize $\psi$ with respect to each unknown component of $f$ by generating $m^2$ equations, one for each unknown (provided m is greater than or equal to n). For example:

$$\frac{\partial \psi}{\partial f_{lm}} = 0 = 2 \sum_{i,k} \left( SIRC_{ik} - \sum_j f_{ij} IRC_{jk} \right) \left( -\sum_j \frac{\partial f_{ij}}{\partial f_{lm}} IRC_{jk} \right)$$

$$0 = \sum_{i,k} \left( SIRC_{ik} - \sum_j f_{ij} IRC_{jk} \right) \left( \sum_j \delta_{il} \delta_{jm} IRC_{jk} \right)$$

$$0 = \sum_k \left( SIRC_{lk} - \sum_j f_{lj} IRC_{jk} \right) (IRC_{mk})$$

$$\sum_k SIRC_{lk} IRC_{mk} = \sum_j f_{lj} \sum_k IRC_{jk} IRC_{mk}$$

The solution for $f$ can be obtained through linear algebra as follows. The resultant set of $M^2$ equations can be written in more succinct matrix form and solved as follows:

$$\sum_k SIRC_{lk} IRC_{mk} = \sum_j f_{lj} \sum_k IRC_{jk} IRC_{mk}$$

$$\overline{\overline{A}} = \overline{\overline{f}} \cdot \overline{\overline{B}}$$

where A and B are matrices with components $$A_{lm} = \sum_k SIRC_{lk} IRC_{mk}$$

$$B_{jm} = \sum_k IRC_{jk} IRC_{mk}$$

hence we may solve for $\overline{\overline{f}}$ $$\overline{\overline{f}} = \overline{\overline{A}} \bullet \overline{\overline{B}}^{-1}$$

provided the inverse of B exists.
Finally, $$\overline{\overline{f}}^{-1} = \overline{\overline{B}} \bullet \overline{\overline{A}}^{-1}$$

Having determined a best fit value for f, that matrix can be used to evaluate the quality of the model and generate the AIRC as follows:

$$\vec{E} = \overrightarrow{SIRC} - \overline{\overline{f}} \bullet \overrightarrow{IRC}$$

In the above, E represents an error vector for our $f$. The basic model evaluation can be applied to additional paired measurements to validate our solution for $f$. The quality of the model can be evaluated by evaluating E for each additional measurement, and by comparing it to the desired physical optics and clinical tolerances of the overall system.

In order to adjust the IRC so as to result in the desired SIRC, we can use $f^{-1}$ so as to generate the AIRC. Hence, when input into the treatment planner, the AIRC will produce the desired treatment for the system:

$$\overrightarrow{AIRC} = \overline{\overline{f}}^{-1} \bullet \overrightarrow{SIRC} = \overline{\overline{f}}^{-1} \bullet \overrightarrow{IRC}.$$

The adjustment in this embodiment produces a AIRC based on a linear combination of the IRC and the co-factors. The combination of wavefront IRC components is generally a cross-coupling which can have physical origins in a number of factors, potentially including the low spatial frequency filtering effects of the flap, the biomechanical and healing effects, tissue transition zone offsets, and the like. Co-factors may represent variables that don't directly enter into the treatment planner module 338 (see FIG. 10A), but which may still have an influence over the outcome. Exemplary co-factors are described above. Adjustments may tend to be highly specific. For example, adjustments may relate to individual physicians or clinics, or sub-populations (for example, high myopes).

Figure 11:
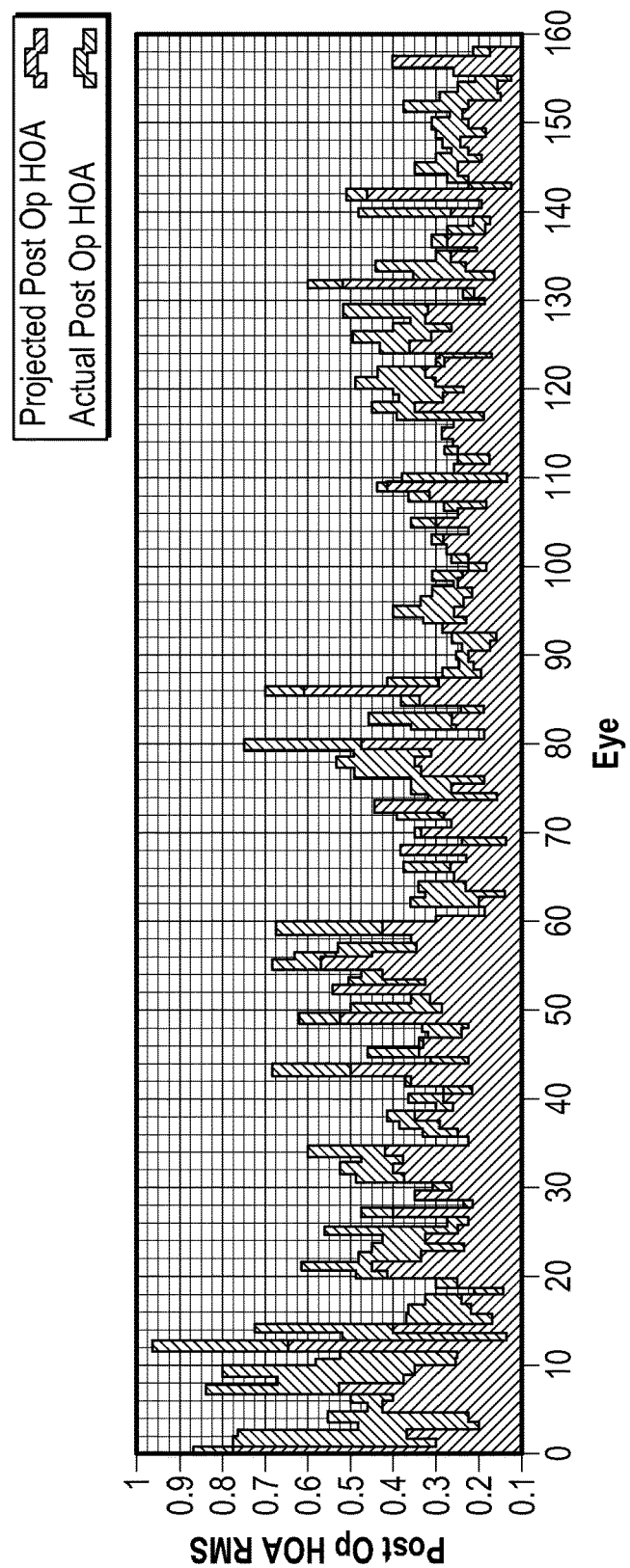
FIG. 11 graphically indicates the surprising benefits in optical accuracy that may be provided by the systems and methods described herein.

Referring now to FIG. 11, modeling based on studies of prior eye treatments indicates surprisingly significant reductions may be provided by the methods and systems described herein. Most, almost all (over 95%) and/or substantially all (over 90%) eyes are projected to exhibit a significant reduction in High-Order Aberrations (HOA).

Figure 12:
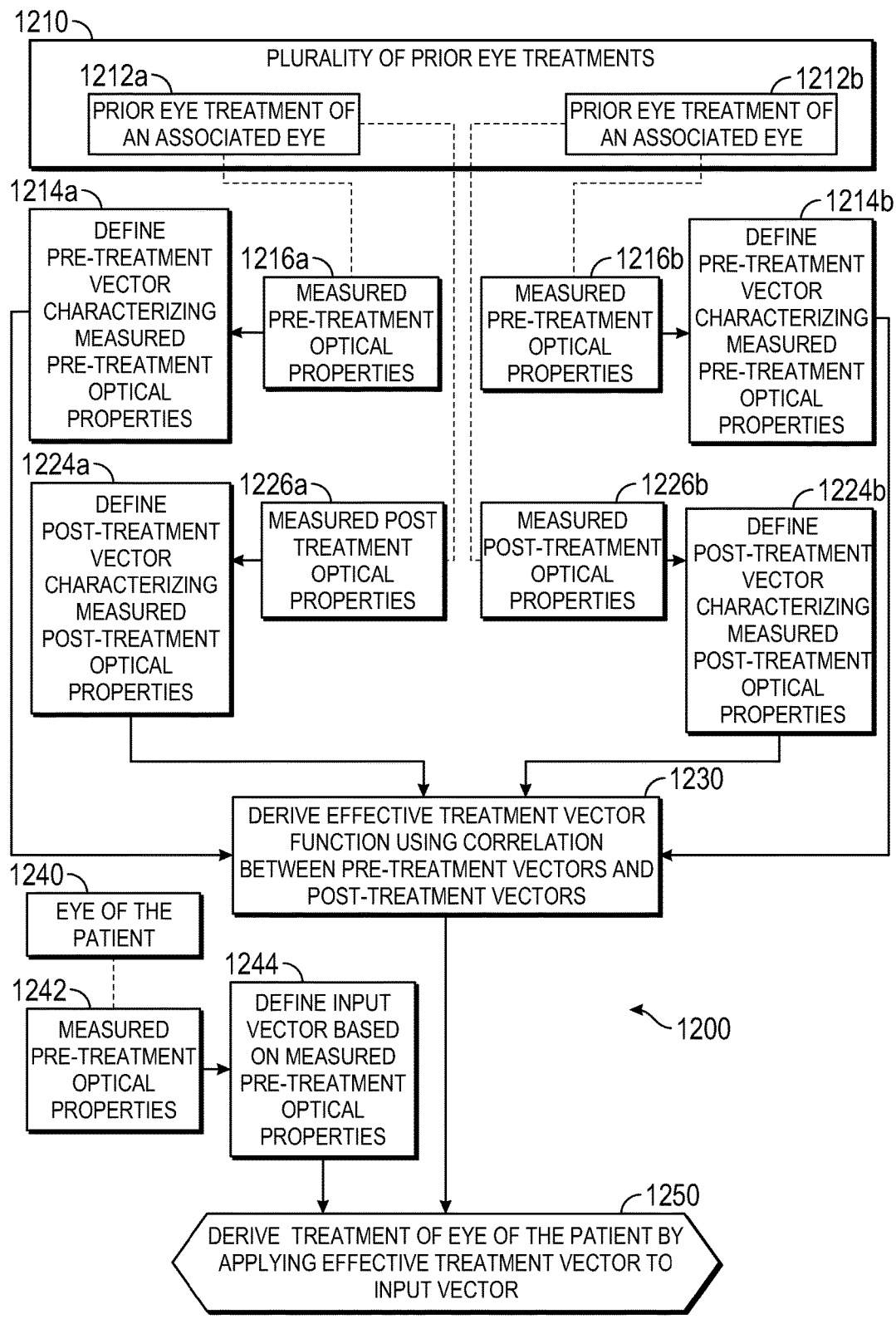
FIG. 12 depicts exemplary aspects of systems and methods according to embodiments of the present invention.

FIG. 12 depicts aspects of a method 1200 for planning a refractive treatment of an eye of a patient, according to embodiments of the present invention. As shown here, method 1200 includes determining an effective treatment vector function based on a plurality of prior eye treatments 1210. As shown here, for individual prior eye treatments of an associated eye 1212a, 1212b (of the plurality of prior eye treatments 1210), exemplary methods involve defining a pre-treatment vector, as depicted by steps 1214a, 1214b, characterizing measured pre-treatment optical properties of the associated eye 1216a, 1216b, respectively. Relatedly, for individual prior eye treatments of an associated eye 1212a, 1212b (of the plurality of prior eye treatments 1210), exemplary methods involve defining a post-treatment vector, as depicted by steps 1224a, 1224b, characterizing measured post-treatment optical properties of the associated eye 1226a, 1226b, respectively. Further, for the plurality of prior eye treatments 1210, the method includes deriving an effective treatment vector function using a correlation between the pre-treatment vectors and the post-treatment vectors, as indicated by step 1230. Method 1200 also includes defining an input vector based on measured pre-treatment optical properties 1242 of the eye of the patient 1240, as depicted by step 1244. Further, method 1200 includes deriving a treatment of the eye of the patient by applying the effective treatment vector function to the input vector, as depicted by step 1250. In some instances, a pre-treatment vector, a post-treatment vector, an effective treatment vector, and/or an input vector can characterize a refraction, a non-refractive cofactor characterizing the patient and/or the treatment setting, and/or optical properties of the eyes.

In some instances, a measured pre-treatment optical property (e.g. 1216a, 1216b, and/or 1242) may include a low order aberration, a high order aberration, a corneal topography measurement, an optical coherence tomography measurement, a corneal keratometry value, or the like. In some instances, a refractive treatment as derived in step 1250 may be for an excimer laser treatment, a femtosecond laser treatment, an intraocular lens treatment, a contact lens treatment, or a spectacle treatment. In some cases, methods further include administering the treatment to the eye of the patient.

In some instances, prior eye treatments 1212a, 1212b, may correspond to a first patient and a second patient, respectively. In some cases, prior eye treatments 1212a, 1212b may correspond to a right eye (OD) and a left eye (OS), respectively. As such, right eyes (or groups of right eyes) and left eyes (or groups of left eyes) can be analyzed separately. Relatedly, data for right eyes (or groups of right eyes) and left eyes (or groups of left eyes) can be transformed to be analyzed simultaneously. In some instances, prior eye treatments 1212a, 1212b may correspond to right eyes only, or alternatively, to left eyes only. Hence, an effective treatment vector function can be derived from on multiple treatments (or information therefrom). In some cases, each prior eye treatment of a plurality of prior eye treatments corresponds to a separate individual. In some cases, each prior eye treatment of a plurality of prior eye treatments corresponds to a previously treated right eye. In some cases, each prior eye treatment of a plurality of prior eye treatments corresponds to a previously treated left eye. Relatedly, when evaluating the eye of the patient 1240, the selected eye (e.g. OD or OS) can correspond to the analyzed eyes from which the effective treatment vector function is derived (e.g. OD or OS). Similarly, the derived treatment can also correspond to the appropriate eye of the patient (e.g. OD or OS).

Figure 13:
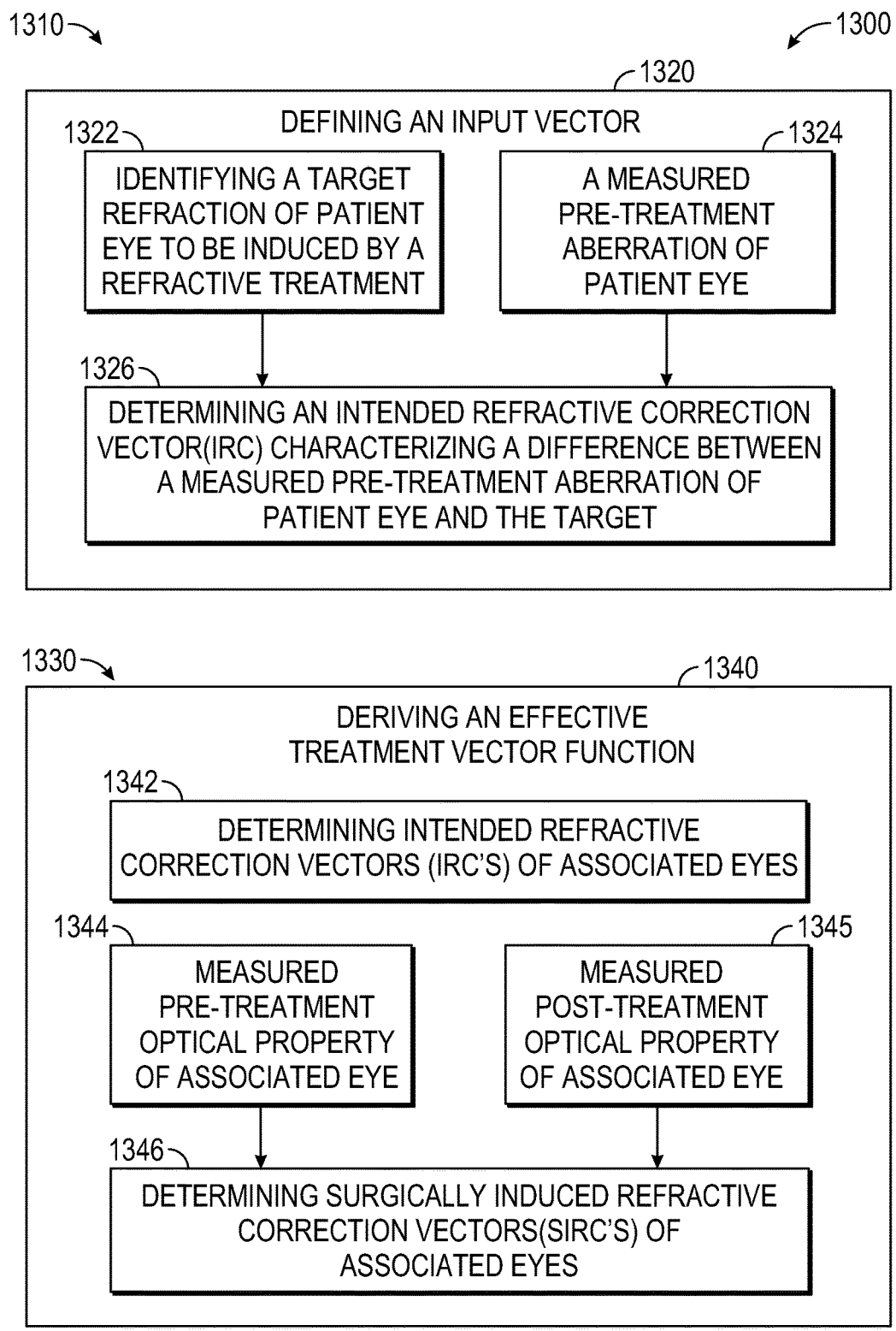
FIG. 13 depicts exemplary aspects of systems and methods according to embodiments of the present invention.

FIG. 13 depicts additional aspects of a process 1310 for defining an input vector 1320, as well as a process 1330 for deriving the effective treatment vector function 1340. As shown here, a procedure for defining an input vector may include identifying a target refraction of the eye of the patient to be induced by the refractive treatment, as indicated by step 1322, and determining an intended refractive correction vector (IRC) characterizing a difference between a measured pre-treatment optical property 1324 of the eye of the patient and the target, as indicated by step 1326. Further, as shown here, a procedure 1330 for deriving the effective treatment vector function from prior treatments may include determining intended refractive correction vectors (IRCs) of associated eyes (e.g. of a plurality of associated eyes), as indicated by step 1342, and determining surgically induced refractive correction vectors (SIRCs) of the associated eyes, as indicated by step 1346. According to some embodiments, each SIRC can characterize a difference between measured pre-treatment optical properties 1344 and post-treatment optical properties 1345 of an associated eye. In some instances, optical properties, SIRCs, and/or IRCs can contain keratometry values, K-values, optical coherence tomography values, corneal topography values, anterior chamber length or depth values, posterior corneal curvature values, axial length values, crystalline lens thickness values, radii of curvature values, tilt values, and the like.

Figure 14:
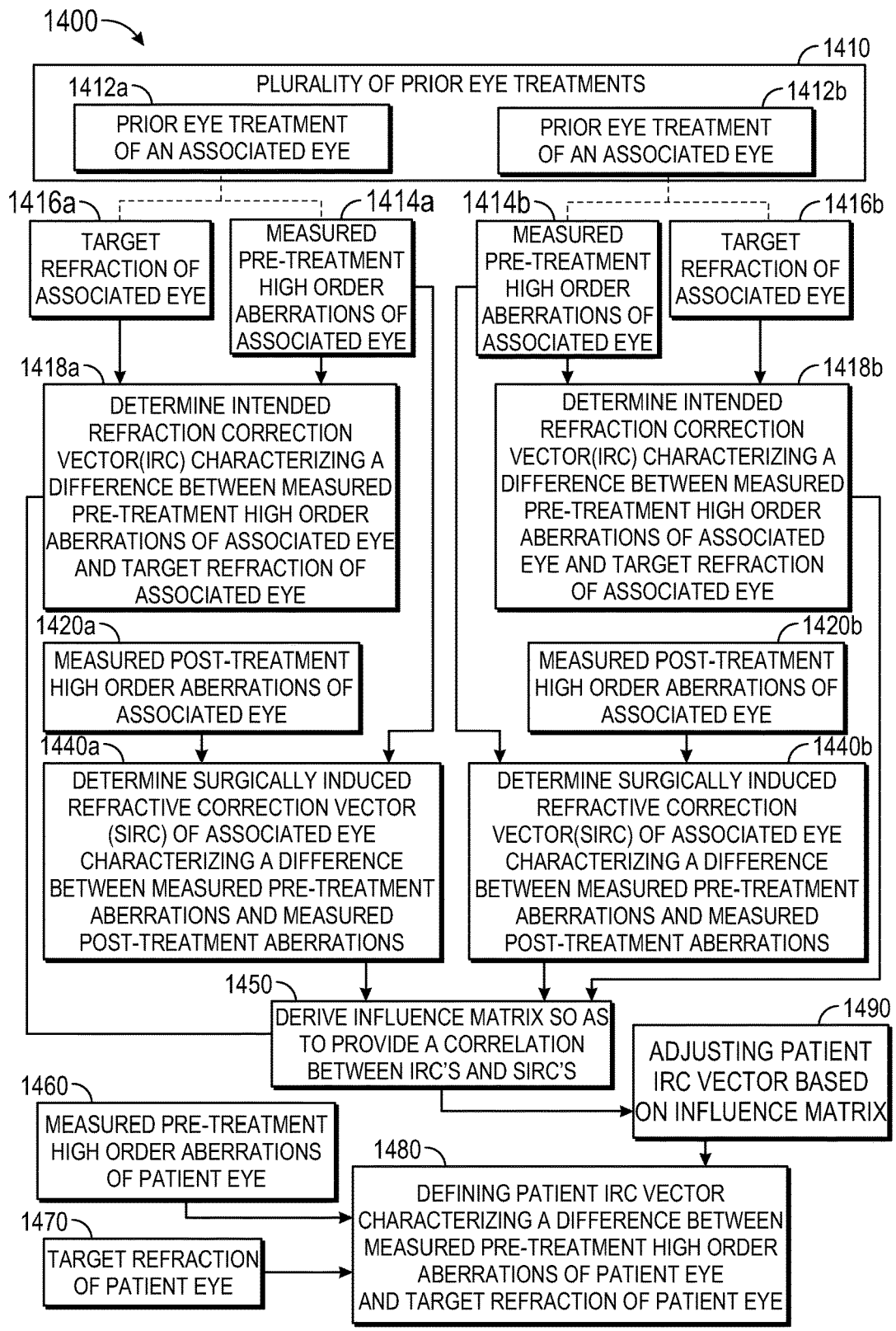
FIG. 14 depicts exemplary aspects of systems and methods according to embodiments of the present invention.

FIG. 14 depicts aspects of a method 1400 for planning a refractive treatment of an eye of a patient, according to embodiments of the present invention. As shown here, method 1400 includes deriving an influence matrix from previously treated eyes, or from a plurality of prior eye treatments 1410. For each prior eye treatment of an associated eye 1412a, 1412b, it is possible to determine an intended refractive correction vector (IRC) and a surgically induced refractive correction vector (SIRC), as follows. As shown here, the method 1400 includes determining an intended refractive correction vector (IRC) characterizing a difference between measured pre-treatment high-order aberrations (or optical properties) 1414a, 1414b of the associated eye and a target refraction of the associated eye 1416a, 1416b as indicated by steps 1418a, 1418b, respectively. Further, the method 1400 includes determining a surgically induced refractive correction vector (SIRC) of the associated eye characterizing a difference between the measured pre-treatment aberrations (or optical properties) 1414a, 1414b and measured post-treatment aberrations (or optical properties) of the associated eye 1420a, 1420b, as indicated by steps 1440a, 1440b, respectively. Methods may also include deriving an influence matrix so as to provide a correlation between the IRCs and the SIRCs, as indicated by step 1450. What is more, methods may include defining a patient IRC vector characterizing a difference between measured pre-treatment high-order aberrations (or optical properties) 1460 of the eye of the patient and a target refraction 1470 of the eye of the patient (e.g. intended surgically induced correction or outcome), as indicated by step 1480. In some cases, a target refraction 1470 may correspond to an emmetropic target. In some cases, a target refraction may correspond to a non-emmetropic target. Further, methods may include adjusting the patient IRC vector based on the influence matrix, as indicated by step 1490. In some cases, an optical property (e.g. 1414a, 1414b, 1420a, 1420b, 1460) may include a low order aberration, a high order aberration, a corneal topography measurement, an optical coherence tomography measurement, and/or a corneal keratometry value. In some cases, methods further include administering a treatment to the eye of the patient based on the patient IRC vector. In some cases, for each prior eye treatment of the associated eye, the IRC can be further determined so as to characterize a difference between measured pre-treatment low order aberrations and target low order aberrations, and so as to characterize a difference between measured pre-treatment corneal topography and target corneal topography. In some cases, for each prior eye treatment of the associated eye, the SIRC can be further determined so as to characterize a difference between the measured pre-treatment low order aberrations and measured post-treatment aberrations, and so as to characterize a difference between measured the pre-treatment corneal topography and measured post-treatment corneal topography. In some cases, a patient IRC vector can be further defined so as to characterize a difference between measured pre-treatment low order aberrations and the target refraction, and so as to characterize a difference between measured pre-treatment topography of the eye and target topography.

In some instances, prior eye treatments 1412a, 1412b, may correspond to a first patient and a second patient, respectively. In some cases, prior eye treatments 1412a, 1412b may correspond to a right eye (OD) and a left eye (OS), respectively. As such, right eyes (or groups of right eyes) and left eyes (or groups of left eyes) can be analyzed separately. Relatedly, data for right eyes (or groups of right eyes) and left eyes (or groups of left eyes) can be transformed to be analyzed simultaneously. In some instances, prior eye treatments 1412a, 1412b may correspond to right eyes only, or alternatively, to left eyes only. Hence, an influence matrix (or SIRC) can be derived from on multiple treatments (or information therefrom). In some cases, each prior eye treatment of a plurality of prior eye treatments corresponds to a separate individual. In some cases, each prior eye treatment of a plurality of prior eye treatments corresponds to a previously treated right eye. In some cases, each prior eye treatment of a plurality of prior eye treatments corresponds to a previously treated left eye. Relatedly, when evaluating the eye of the patient 1460, the selected eye (e.g. OD or OS) can correspond to the analyzed eyes from which the influence matrix (or SIRC) is derived (e.g. OD or OS). Similarly, the adjusted patient IRC vector can also correspond to the appropriate eye of the patient (e.g. OD or OS).

Figure 15:
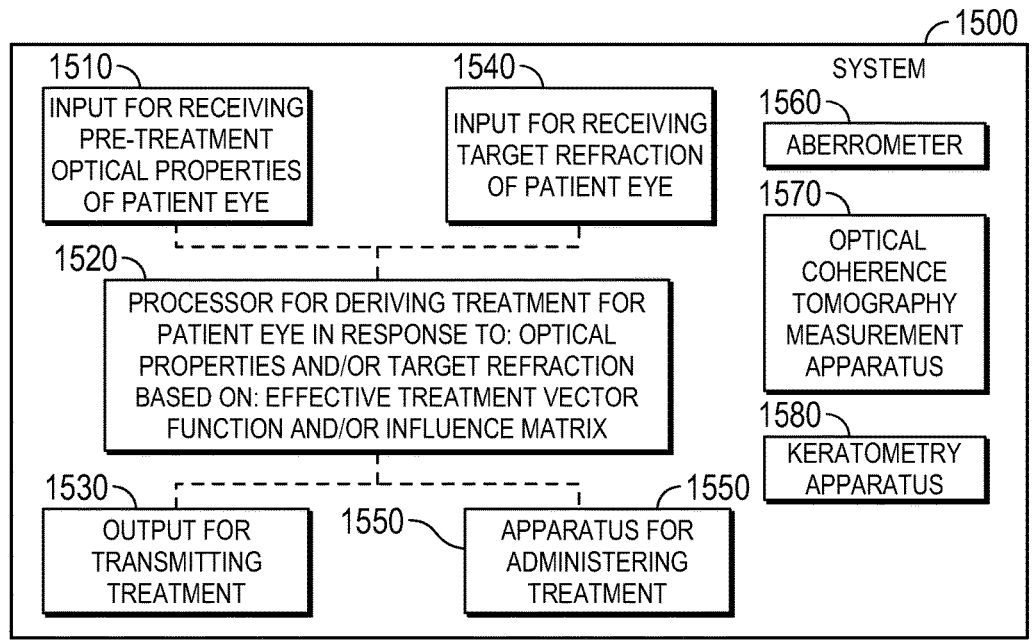
FIG. 15 depicts exemplary aspects of systems and methods according to embodiments of the present invention.

FIG. 15 depicts aspects of a system 1500 for planning or deriving a refractive treatment of an eye of a patient, according to embodiments of the present invention. As shown here, system 1500 includes an input 1510 for receiving pre-treatment optical properties of the eye of the patient, a processor 1520 coupled to the input, and an output 1530 coupled to the processor. In some instances, the processor 1520 is configured to derive the treatment of the eye of the patient in response to the optical properties of the eye of the patient, by applying an effective treatment vector function. In some cases, the effective treatment vector function can be derived from, for each of a plurality of prior eye treatments, a correlation between a pre-treatment vector characterizing optical properties of the associated eye before treatment, and a post-treatment vector characterizing post-treatment optical properties of the associated eye. In some instances, the output 1530 can be configured to transmit the treatment to facilitate improving refraction of the eye of the patient.

According to some embodiments, system 1500 may include an input 1540 for receiving a target refraction of a patient eye. In some embodiments, system 1500 may include or be coupled with an apparatus 1550, such as a laser delivery system, for administering a treatment to a patient. As shown here, system 1500 may also include, or be coupled with, an aberrometer 1560. In some cases, the aberrometer 1560 may be configured to sense low order aberrations of the eye and the high-order aberrations of an eye. Such low and high-order aberrations may be transmitted to or received by the processor 1520. In some cases, the aberrometer 1560 may be configured to sense corneal topography of the eye. Such corneal topography can be transmitted to or received by the processor 1520. System 1500 may also include, or be coupled with, an optical tomography measurement apparatus 1570. In some cases, the optical tomography measurement apparatus 1570 can be configured to detect optical properties of the eye. Such optical properties may be transmitted to or received by the processor 1520. System 1500 may also include, or be coupled with, a keratometry apparatus 1580. In some cases, the keratometry apparatus 1580 can be configured to detect optical properties of the eye. Such optical properties may be transmitted to or received by the processor 1520.

Typically, the keratometry apparatus 1580 can be used to measure or evaluate the radius of curvature of the cornea. The keratometry apparatus 1580 may be, for example, a keratometer or ophthalmometer that measures the curvature of the anterior corneal surface. In a keratometry technique, the anterior corneal surface can be considered as a specular reflector. A ring can be placed in front of the eye, and the cornea, in reflection, can form a virtual image of the ring below its surface, such that the virtual image is the first Purkinje image of the ring. The size of this image can be related to the corneal radius of curvature (R), according to the equation R=2dy/h, where h is the radius of the ring object, y is the radius of the ring image, and d is the distance between the object and image. Using a keratometric index of refraction, it is possible to convert the corneal radius to corneal power. In this way, keratometry can be used to evaluate corneal power an anterior corneal surface measurement. In some cases, the ring is an elliptical shape having major and minor axes (e.g. where corneal astigmatism is present). Keratometry can be measured along the two orthogonal meridians, to provide maximum and minimum corneal power, and such extrema can be presented as corneal K's, or K-values. In some aspects, K-values can be used to quantify the central steepness of the cornea. Hence, systems may optionally include or use information obtained by keratometry devices (e.g. curvature values) and/or topography devices (e.g. elevation values). In some cases, topography information may be used to determine or approximate K-values.

Figure 16:
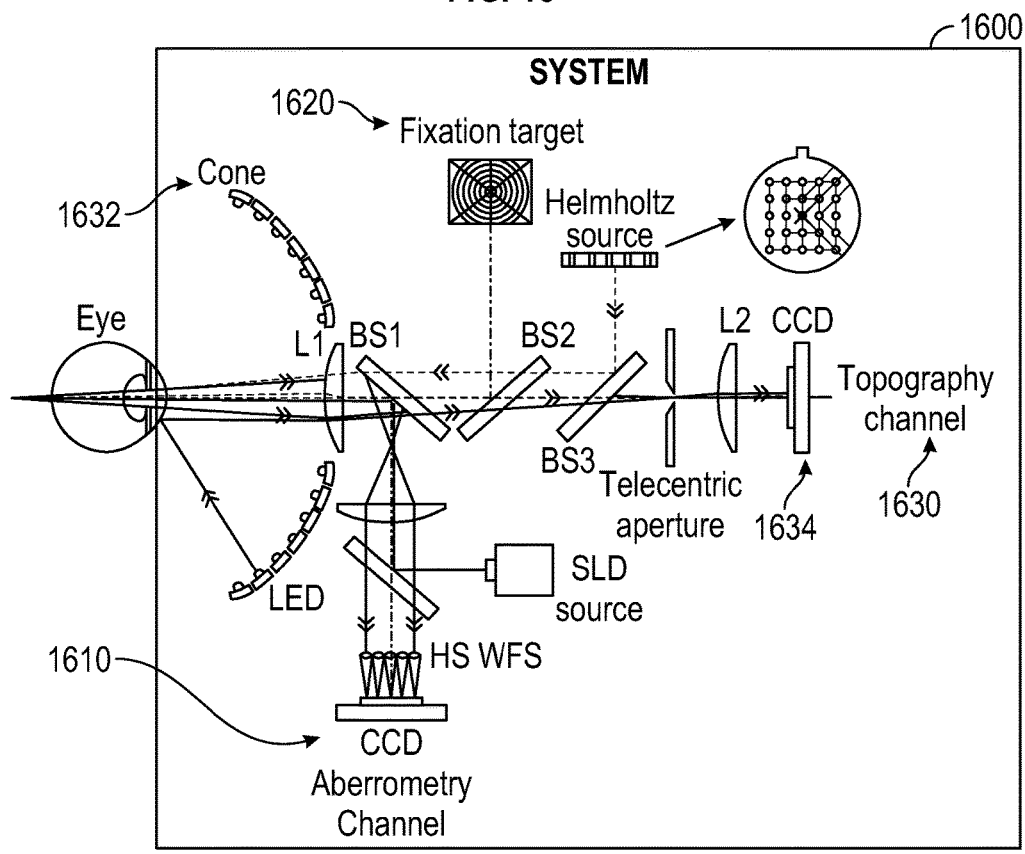
FIG. 16 depicts exemplary aspects of systems and methods according to embodiments of the present invention.

FIG. 16 depicts aspects of a system or apparatus 1600 for administering a refractive treatment to an eye of a patient, according to embodiments of the present invention. As shown here, system 1600 combines aberrometry and corneal topography measurements. System 1600 includes a wavefront sensor component 1610, which may be a Hartman-Shack (HS WFS) type aberrometer. In some cases, wavefront sensor component 1610 includes a high definition wavefront aberrometer, such as the COAS-HD™ Model 2800. System 1600 also includes a fixation target 1620, which may be generated by a microdisplay. As shown here, system 1600 also includes a corneal topography apparatus 1630. In some instances, topography apparatus 1630 may be used to obtain K-values. Operation of the corneal topography apparatus 1630 may involve measuring the position of Purkinje I reflections on an array of light sources appropriately spaced on a cone-like surface 1632. The optical arrangement can create a grid of rectangularly and uniformly spaced Purkinje I reflections, that can be observed by a CCD detector 1634 (e.g. topography channel), for example when a calibration surface of average corneal dimensions is measured. The cone-like surface 1632 can be back illuminated by a Lambertian reflectance screen using 780 nm LEDs. This uniform light field can then be masked by an optically thick screen with appropriately spaced and angled fenestrations. This produces sources with a narrow forward emission primarily directed towards the focal plane of the anterior cornea and improves photometric efficiency of the instrument. The corneal gradient at each sample point can be determined by analyzing the translation of the spot position in two (x and y) directions. Translation of the spot position can allow calculation of the ray angle with respect to the surface normal at the sample location. As the ingoing ray angle is known from the instrument geometry, the gradient of the corneal surface is measured. Integration and an iterative search algorithm (based on Fermat's principle) allows reconstruction of the elevation data. The distance between the eye under measurement and the first optical element in the system can be measured in order to determine the radius of curvature. In the instrument, the distance can be measured by noting that the radius of curvature calculated from the Helmholtz spots (HHS) is independent of the eye position (since the light is projected through the collecting lens). For the corneal topography (CT) cone spots the pattern may depend on both the radius of curvature and the eye position. The position where the HHS pattern matches the CT pattern can yield the correct distance. The measurement of the corneal gradient can be in two directions. The corneal topography measurement data can be mapped onto the same axis as used for the aberrometry measurement (e.g. line of sight, or LOS), and the results can be presented to the operator following this mapping process. Sampling at the cornea can be 215 microns square (e.g. for an 8 mm radius of curvature cornea), and the sampling pattern may be slightly less dense in the central corneal region. The aberrometry and the corneal topography measurements may not be exactly simultaneous. In some cases, the time separation between these measurements is less than a tenth of a second. Each measurement can include multiple images, including for example a wavefront spot image, a corneal topography spot image, a scotopic iris (SI), and a photopic iris (PI). The latter three images (CT, SI and PI) can be recorded with the same camera but with different illumination. Both the aberrometry and topography systems may use a prerecorded reference to subtract any small residual errors in the optical systems. These can be optically recorded using ideal wavefront and cornea surface standards. The instrument's software can map the aberrometry and topography data sets onto a mutual coordinate system, and by exporting the raw corneal elevation data it is possible to retain the CT data in a format with its coordinate system centered along the VK axis.

In a patient having high cylinder, a standard surgery may improve the cylinder without improving the sphere. Relatedly, a standard surgery may increase the amount of high order aberration in a patient. However, various couplings have been determined to exist between certain low order aberrations, high order aberrations, and other optical properties. Such couplings can be used for improving final visual acuity, and other optical performance characteristics. For example, couplings have been observed between cylinder (pre-operative) and net sphere (post-operative). Hence, in some cases, both sphere and cylinder terms may be included in the analysis. For example, the multivariate techniques disclosed herein can be used to generate a treatment vector and/or influence matrix that corrects or compensates for this coupling, as well as those for the higher order terms. In some cases, this may involve a treatment vector that corrects or compensates for the coupling by adjusting a cylinder value so as to achieve a desired effect for sphere. Thus, according to embodiments of the present invention, it is possible to use an influence matrix or other effective treatment vector function to identify and/or compensate for a coupling between cylinder and sphere, and hence provide a solution that increases the overall accuracy of treatment. In another example, optical data from patients was analyzed, and correlations between cylinder (e.g. pre-treatment) and sphere (e.g. post-treatment) increased when keratometry data (e.g. pre-treatment K-values) was also considered. For example, a correlation coefficient of about 19% between cylinder and sphere was observed without using keratometry data, and a correlation coefficient of about 59% was observed when using keratometry data. In many cases, treatments were applied using the same treatment instrument, and preoperative and postoperative data was obtained using the same diagnostic instrument. According to embodiments of the present invention, improved correlations can be obtained when considering an array of optical properties, for example low order aberrations, high order aberrations, corneal topography measurements, optical coherence tomography measurements, corneal keratometry values, and related elements such as anterior and/or posterior chamber length or depth values, anterior and/or posterior corneal curvature values, axial length values, crystalline lens thickness values, radii of curvature values, tilt values (e.g. natural lens), lens decentration values (e.g. natural lens), induced astigmatism (or related corneal incision parameters such as incision orientation), pupil centration or decentration values (e.g. location of pupil center), pupil state (e.g. dilation), lighting levels (e.g. mesopic or photopic), physician-specific factors (e.g. surgical technique, previous history), planned treatment data (e.g. planned induced astigmatism), resulting treatment data (e.g. outcome or changed observed following treatment), Purkinje images, corneal flap dimension data (e.g. flap diameter or area), corneal hydration data, and the like. Such techniques can be applied in the context of laser-assisted in situ keratomileusis (LASIK), photorefractive keratectomy (PRK), laser-assisted sub-epithelial keratectomy (LASEK), radial keratometry, arcuate keratometry, and other laser refractive and/or corneal surgeries, as well as for intra-ocular lens treatments, contact lenses, spectacles, and the like.

In another example, optical parameter measurements were obtained directly from diagnostic instruments, in the absence of any physician adjustments, and similar correlations were observed. In some cases, for each diopter of cylinder, a corresponding ⅛ diopter of sphere was observed.

Hence, in a patient having a high cylinder value (e.g. −3 D, −4 D), a corresponding difference in sphere of about ⅜ D or ⅘ D was observed.

In some instances, strong couplings have been observed between K-values and one or more higher order aberrations. Hence, for example, it is possible to determine a correction or adjustment in K-values that would result in a desired result for spherical aberration. In this way, a result may be more predictable when considering both the K-values and the aberrations. For example, the multivariate techniques disclosed herein can be used to generate a treatment vector and/or influence matrix that corrects or compensates for this coupling. In some cases, this may involve a treatment vector that corrects or compensates for the coupling by adjusting a K-value so as to achieve a desired effect for spherical aberration.

In some cases, it may be possible to reduce high order aberrations that may otherwise be induced as a result of surgery. For example, where a particular corneal incision or relaxation cut may induce an amount of cylinder or astigmatism, it may be possible to plan an ocular treatment that incorporates the formation of such incisions, before or in addition to performing the surgery. In this way, it may be possible to use techniques described herein to compensate in advance for the effect of a surgery.

Embodiments of the present invention further encompass systems and methods for collecting, storing, analyzing, and transmitting information related to pre-operative and post-operative parameters. For example, when a physician or operator performs pre-operative and/or post-operative measurements of a patient at the doctor's office or hospital, such information can be transmitted to a computer system. A processor of the computer system may be configured to analyze that information and build a nomogram for the physician. Similarly, information from a plurality of physicians or information from a plurality of patients can be provided to an analyzed by the computer processor. The computer process may also be configured to determine influence matrices, effective treatment vector functions, and/or patient-specific treatment parameters using the techniques described elsewhere herein. In some cases, it may be possible to selectively chose which parameters are used when determining the influence matrices, effective treatment vector functions, and/or patient-specific treatment parameters. For example, a particular physician may wish to determine a patient treatment parameter without using data associated with a particular parameter. Likewise, a physician may wish to use only data that is associated with a particular range of values for a particular parameter (e.g. selecting data only for eyes that are treated in a dry climate). In some cases, physicians may obtain treatment output from the computer system, and adjust that treatment output before providing the patient with the treatment. Optionally, such adjustments may be transmitted to the computer system for additional analysis. Further optionally, treatment information provided by the computer may be based on or factor in such adjustments. In some cases, techniques may include providing a physician with a predicted outcome based on a suggested treatment, and the physician may compare that predicted outcome with the actual outcome obtained. Hence, techniques may involve obtaining measured pre-treatment and/or post-treatment optical properties of an associated eye, or other related parameters as discussed elsewhere herein, optionally obtained from database, such as a database located in a doctor office, hospital, or some other centralized location (optionally networked with multiple doctor office and/or hospital databases or computer systems). In some instance, embodiments encompass techniques for tracking recommended procedures as well as procedures eventually performed based on recommended procedures, for comparing or analyzing such recommended and performed procedures, for archiving such recommended and performed procedures (and their comparisons), and for adjusting recommendations based on the comparisons.

With regard to arcuate corneal surgeries, incisions can be used to relax corneal astigmatism, and related techniques can be used in IOL surgery. For example, a surgeon may place the corneal incision on the steep axis of the cornea to relax the corneal astigmatism and reduce the need for toric IOLs in patients with less than 1 Diopter of astigmatism. In some cases, the preoperative astigmatism magnitude and axis, the number, angular arc and radial position of incision(s) relative to the optical zone, and age can be considered as parameters for this type of surgery. Use of femtosecond (FS) lasers in arcuate surgery can increase the precision with which the incisions can be made and may result in better outcomes for patients. In addition, FS lasers can be applied to correct corneal astigmatism following corneal transplants. As in the case of other refractive surgeries, it is possible to apply the techniques described herein to improve patient outcomes by using historical outcome data. In the case of arcuate surgery, it is possible to use the parameters noted above (e.g. preoperative astigmatism magnitude and axis, the number, angular arc and radial position of incision(s) relative to the optical zone, and age) in a pre-operative vector. More advanced predictive modeling may include corneal topography based keratometry values, pachymetry and corneal hydration when available to improve the model accuracy. The case of FS arcuate laser surgery may add other options to the incision characteristics as well. These may include partial incisions that don't perforate or break the surface of the cornea, profiled incisions rather than purely normal to the cornea, and incisions other than straight lines and circular arcs (e.g. undulating wave-like or squiggly lines). In some cases, techniques may include completely intrastromal incisions or disruptions. In some cases, techniques may include incisions or disruptions which reach a corneal surface. In some cases, the parameters describing the details of the incision and preoperative parameters may be included in the pre-operative vector.

All patents, patent applications, journal articles, technical references, and the like mentioned herein are hereby incorporated herein by reference for all purposes.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While the exemplary embodiments have been described in some detail for clarity of understanding and by way of example, a number of adaptations, changes, and modifications will be obvious to those of skill in the art. Hence, the scope of the present invention is solely limited by the claims associated herewith.

What is claimed is:

1. A method, comprising:
   measuring a set of pre-treatment values for a plurality of optical properties of an eye of a current patient, including measuring with a wavefront measurement device pre-treatment values for at least some high order aberrations of the eye of the current patient which have an order greater than two;
   establishing a set of target post-treatment values for the plurality of optical properties of the eye of the current patient, including target post-treatment values for the at least some high order aberrations of the eye of the current patient which have an order greater than two;
   determining a set of intended refractive corrections to be applied to the eye as differences between the target post-treatment values for the plurality of optical properties of the eye of the current patient and the pre-treatment values for the plurality of optical properties of the eye of the current patient, wherein the set of intended refractive corrections to be applied to the eye of the current patient include intended refractive corrections to the at least some high order aberrations of the eye of the current patient which have an order greater than two;
   receiving sets of intended refractive corrections to be applied to eyes of previous patients, and sets of measured surgery induced refractive corrections of the eyes of the previous patients from previous surgeries on the eyes of the previous patients;
   producing an effective treatment function which minimizes differences between: (1) the sets of intended refractive corrections to be applied to eyes of previous patients, and (2) the sets of measured surgery induced refractive corrections of the eyes of the previous patients from the previous surgeries on the eyes of the previous patients;
   applying the effective treatment function, physician adjustments, and chromatic and cosine corrections to the intended refractive corrections to be applied to the eye of the current patient to produce a set of adjusted intended refractive corrections to be applied to the eye of the current patient, including values for the at least some high order aberrations of the eye of the current patient which have an order greater than two; and
   performing laser treatment of the eye of the current patient using the set of adjusted intended refractive corrections to be applied to the eye of the current patient so as to transform the eye of the current patient to exhibit the target post-treatment values for the plurality of optical properties of the eye of the current patient, including the at least some high order aberrations of the eye of the current patient which have an order greater than two.

2. The method of claim 1, further comprising measuring pre-treatment corneal topography data for the eye of the current patient and including the measured pre-treatment corneal topography data in the set of pre-treatment values for the plurality of optical properties of the eye of the current patient.

3. The method of claim 1, further comprising measuring a set of post-treatment values for the optical properties of the eye of the current patient after the laser treatment, including the at least some high order aberrations of the eye of the current patient which have an order greater than two, and producing therefrom a set of measured induced refractive corrections for the eye of the current patient as a result of the laser treatment.

4. The method of claim 3, further comprising, after the laser treatment of the eye of the current patient:
   including the set of adjusted intended refractive corrections to be applied to the eye of the current patient in the sets of intended refractive corrections to be applied to eyes of previous patients; and
   including the set of measured induced refractive corrections for the eye of the current patient as a result of the laser treatment in the sets of measured surgery induced refractive corrections of the eyes of the previous patients from the previous surgeries on the eyes of the previous patients.

5. The method of claim 1, wherein a plurality of values of the set of adjusted intended refractive corrections to be applied to the eye of the current patient are each altered by a plurality of values of the effective treatment function.

6. A method, comprising:
   measuring, with a wavefront measurement device, a set of pre-treatment values for at least some high order aberrations of the eye of the current patient which have an order greater than two;
   establishing a set of target post-treatment values for the at least some high order aberrations of the eye of the current patient which have an order greater than two;
   determining a set of intended refractive corrections to be applied to the eye of the current patient as differences between the target post-treatment values for the at least some high order aberrations of the eye of the current patient and the pre-treatment values for the at least some high order aberrations of the eye of the current patient;
   receiving an effective treatment function which minimizes differences between: (1) sets of intended refractive corrections to be applied to eyes of previous patients, and (2) sets of measured surgery induced refractive corrections of the eyes of the previous patients from the previous surgeries on the eyes of the previous patients;
   applying the effective treatment function, physician adjustments, and chromatic and cosine corrections to the intended refractive corrections to be applied to the eye of the current patient to produce a set of adjusted intended refractive corrections to be applied to the eye of the current patient, including values for the at least some high order aberrations of the eye of the current patient which have an order greater than two; and
   performing laser treatment of the eye of the current patient using the set of adjusted intended refractive corrections to be applied to the eye of the current patient so as to transform the eye of the current patient to exhibit the target post-treatment values for the at least some high order aberrations of the eye of the current patient.

7. The method of claim 6, further comprising measuring a set of post-treatment values for the optical properties of the eye of the current patient after the laser treatment, including the at least some high order aberrations of the eye of the current patient which have an order greater than two, and producing therefrom a set of measured induced refractive corrections for the eye of the current patient as a result of the laser treatment.

8. The method of claim 7, further comprising, after the laser treatment of the eye of the current patient:
   including the set of adjusted intended refractive corrections to be applied to the eye of the current patient in the sets of intended refractive corrections to be applied to eyes of previous patients; and including the set of measured induced refractive corrections for the eye of the current patient as a result of the laser treatment in the sets of measured surgery induced refractive corrections of the eyes of the previous patients from the previous surgeries on the eyes of the previous patients.

9. The method of claim 6, wherein a plurality of values of the set of adjusted intended refractive corrections to be applied to the eye of the current patient are each altered by a plurality of values of the effective treatment function.

10. A method, comprising:
    measuring, with a wavefront measurement device, a set of pre-treatment values for aberrations of the eye of the current patient, including low order aberrations which have an order of two or less and at least some high order aberrations which have an order greater than two;
    establishing a set of target post-treatment values for the aberrations of the eye of the current patient, including the low order aberrations which have an order of two or less and the at least some high order aberrations which have an order greater than two;
    determining a set of intended refractive corrections to be applied to the eye as differences between the target post-treatment values for the aberrations of the eye of the current patient, including the low order aberrations which have an order of two or less and the at least some high order aberrations which have an order greater than two, and the pre-treatment values for the aberrations of the eye of the current patient, including the low order aberrations which have an order of two or less and the at least some high order aberrations which have an order greater than two, wherein the set of intended refractive corrections to be applied to the eye of the current patient include intended refractive corrections to the low order aberrations which have an order of two or less and the at least some high order aberrations which have an order greater than two;
    receiving sets of intended refractive corrections to be applied to eyes of previous patients, and sets of measured surgery induced refractive corrections of the eyes of the previous patients from previous surgeries on the eyes of the previous patients;
    producing an effective treatment function which minimizes differences between: (1) the sets of intended refractive corrections to be applied to eyes of previous patients, and (2) the sets of measured surgery induced refractive corrections of the eyes of the previous patients from the previous surgeries on the eyes of the previous patients;
    applying the effective treatment function, physician adjustments, and chromatic and cosine corrections to the intended refractive corrections to be applied to the eye of the current patient to produce a set of adjusted intended refractive corrections to be applied to the eye of the current patient, including adjusted values for the intended refractive corrections to the low order aberrations which have an order of two or less and the at least some high order aberrations which have an order greater than two; and
    performing laser treatment of the eye of the current patient using the set of adjusted intended refractive corrections to be applied to the eye of the current patient so as to transform the eye of the current patient to exhibit the target post-treatment values for the aberrations of the eye of the current patient, including the low order aberrations which have an order of two or less and the at least some high order aberrations which have an order greater than two.

11. The method of claim 10, further comprising measuring a set of post-treatment values for the aberrations of the eye of the current patient, including the low order aberrations which have an order of two or less and the at least some high order aberrations which have an order greater than two, and producing therefrom a set of measured induced refractive corrections for the eye of the current patient as a result of the laser treatment.

12. The method of claim 11, further comprising, after the laser treatment of the eye of the current patient:
    including the set of adjusted intended refractive corrections to be applied to the eye of the current patient in the sets of intended refractive corrections to be applied to eyes of previous patients; and
    including the set of measured induced refractive corrections for the eye of the current patient as a result of the laser treatment in the sets of measured surgery induced refractive corrections of the eyes of the previous patients from the previous surgeries on the eyes of the previous patients.

13. The method of claim 10, wherein a plurality of values of the set of adjusted intended refractive corrections to be applied to the eye of the current patient are each altered by a plurality of values of the effective treatment function.

14. A system, comprising:
    an apparatus configured to measure pre-treatment optical properties of the eye of the current patient, the apparatus including a wavefront measurement device configured to measure at least pre-treatment high order aberrations of the eye of the current patient which have an order greater than two;
    a processor coupled to the wavefront measurement device, the processor having an input configured to receive sets of intended refractive corrections to be applied to eyes of previous patients, and sets of measured surgery induced refractive corrections of the eyes of the previous patients from previous surgeries on the eyes of the previous patients, wherein the processor is configured to:
        establish a set of target post-treatment values for the plurality of optical properties of the eye of the current patient, including target post-treatment values for the at least some high order aberrations of the eye of the current patient which have an order greater than two,
        determine a set of intended refractive corrections to be applied to the eye as differences between the target post-treatment values for the plurality of optical properties of the eye of the current patient and the pre-treatment values for the plurality of optical properties of the eye of the current patient, wherein the set of intended refractive corrections to be applied to the eye of the current patient include intended refractive corrections to the at least some high order aberrations of the eye of the current patient which have an order greater than two,
        produce an effective treatment function which minimizes differences between: (1) the sets of intended refractive corrections to be applied to eyes of previous patients, and (2) the sets of measured surgery induced refractive corrections of the eyes of the previous patients from the previous surgeries on the eyes of the previous patients, and
        apply the effective treatment function, physician adjustments, and chromatic and cosine corrections to the intended refractive corrections to be applied to the eye of the current patient to produce a set of adjusted intended refractive corrections to be applied to the eye of the current patient, including values for the at least some high order aberrations of the eye of the current patient which have an order greater than two; and a laser system configured to perform laser treatment of the eye of the current patient using the set of adjusted intended refractive corrections to be applied to the eye of the current patient so as to transform the eye of the current patient to exhibit the target post-treatment values for the plurality of optical properties of the eye of the current patient, including the at least some high order aberrations of the eye of the current patient which have an order greater than two.

15. The system of claim 14, further comprising a corneal topographer configured to measure pre-treatment corneal topography data for the eye of the current patient and including the measured pre-treatment corneal topography data in the set of pre-treatment values for the plurality of optical properties of the eye of the current patient.

16. The system of claim 14, wherein the system is further configured to measure a set of post-treatment values for the optical properties of the eye of the current patient after the laser treatment, including the at least some high order aberrations of the eye of the current patient which have an order greater than two, and to produce therefrom a set of measured induced refractive corrections for the eye of the current patient as a result of the laser treatment.

17. The system of claim 16, wherein the system is further configured to, after the laser treatment of the eye of the current patient:
  include the set of adjusted intended refractive corrections to be applied to the eye of the current patient in the sets of intended refractive corrections to be applied to eyes of previous patients; and
  include the set of measured induced refractive corrections for the eye of the current patient as a result of the laser treatment in the sets of measured surgery induced refractive corrections of the eyes of the previous patients from the previous surgeries on the eyes of the previous patients.

18. The system of claim 14, wherein a plurality of values of the set of adjusted intended refractive corrections to be applied to the eye of the current patient are each altered by a plurality of values of the effective treatment function.

19. A system, comprising:
  a wavefront measurement device configured to measure a set of pre-treatment high order aberrations of the eye of the current patient which have an order greater than two;
  a processor coupled to the wavefront measurement device, the processor having an input configured to receive an effective treatment function which minimizes differences between: (1) sets of intended refractive corrections to be applied to eyes of previous patients, and (2) sets of measured surgery induced refractive corrections of the eyes of the previous patients from previous surgeries on the eyes of the previous patients, wherein the processor is configured to:
    establish a set of target post-treatment values for the at least some high order aberrations of the eye of the current patient which have an order greater than two,
    determine a set of intended refractive corrections to be applied to the eye of the current patient as differences between the target post-treatment values for the at least some high order aberrations of the eye of the current patient and the pre-treatment values for the at least some high order aberrations of the eye of the current patient, and
    apply the effective treatment function, physician adjustments, and chromatic and cosine corrections to the intended refractive corrections to be applied to the eye of the current patient to produce a set of adjusted intended refractive corrections to be applied to the eye of the current patient, including values for the at least some high order aberrations of the eye of the current patient which have an order greater than two; and
  a laser system configured to perform laser treatment of the eye of the current patient using the set of adjusted intended refractive corrections to be applied to the eye of the current patient so as to transform the eye of the current patient to exhibit the target post-treatment values for the at least some high order aberrations of the eye of the current patient.

20. The system of claim 19, wherein the wavefront measurement device is further configured to measure a set of post-treatment values for the high order aberrations of the eye of the current patient which have an order greater than two after the laser treatment, and the processor is further configured to produce therefrom a set of measured induced refractive corrections for the eye of the current patient as a result of the laser treatment.

21. The system of claim 20, wherein the system is further configured to, after the laser treatment of the eye of the current patient:
  include the set of adjusted intended refractive corrections to be applied to the eye of the current patient in the sets of intended refractive corrections to be applied to eyes of previous patients; and
  include the set of measured induced refractive corrections for the eye of the current patient as a result of the laser treatment in the sets of measured surgery induced refractive corrections of the eyes of the previous patients from the previous surgeries on the eyes of the previous patients.

22. The system of claim 19, wherein a plurality of values of the set of adjusted intended refractive corrections to be applied to the eye of the current patient are each altered by a plurality of values of the effective treatment function.

23. A system, comprising:
  a wavefront measurement device configured to measure a set of pre-treatment values for aberrations of the eye of the current patient, including low order aberrations which have an order of two or less and at least some high order aberrations which have an order greater than two;
  a processor coupled to the wavefront measurement device, the processor having an input configured to receive sets of intended refractive corrections to be applied to eyes of previous patients, and sets of measured surgery induced refractive corrections of the eyes of the previous patients from previous surgeries on the eyes of the previous patients, wherein the processor is configured to:
    establish a set of target post-treatment values for the aberrations of the eye of the current patient, including the low order aberrations which have an order of two or less and the at least some high order aberrations which have an order greater than two, determine a set of intended refractive corrections to be applied to the eye as differences between the target post-treatment values for the aberrations of the eye of the current patient, including the low order aberrations which have an order of two or less and the at least some high order aberrations which have an order greater than two, and the pre-treatment values for the aberrations of the eye of the current patient, including the low order aberrations which have an order of two or less and the at least some high order aberrations which have an order greater than two, wherein the set of intended refractive corrections to be applied to the eye of the current patient include intended refractive corrections to the low order aberrations which have an order of two or less and the at least some high order aberrations which have an order greater than two, produce an effective treatment function which minimizes differences between: (1) the sets of intended refractive corrections to be applied to eyes of previous patients, and (2) the sets of measured surgery induced refractive corrections of the eyes of the previous patients from the previous surgeries on the eyes of the previous patients, and apply the effective treatment function, physician adjustments, and chromatic and cosine corrections to the intended refractive corrections to be applied to the eye of the current patient to produce a set of adjusted intended refractive corrections to be applied to the eye of the current patient, including adjusted values for the intended refractive corrections to the low order aberrations which have an order of two or less and the at least some high order aberrations which have an order greater than two; and a laser system configured to perform laser treatment of the eye of the current patient using the set of adjusted intended refractive corrections to be applied to the eye of the current patient so as to transform the eye of the current patient to exhibit the target post-treatment values for the aberrations of the eye of the current patient, including the low order aberrations which have an order of two or less and the at least some high order aberrations which have an order greater than two.

24. The system of claim 23, wherein the wavefront measurement device is further configured to measure a set of post-treatment values for the aberrations of the eye of the current patient, including the low order aberrations which have an order of two or less and the at least some high order aberrations which have an order greater than two, and the processor is further configured to produce therefrom a set of measured induced refractive corrections for the eye of the current patient as a result of the laser treatment.

25. The system of claim 24, wherein the system is further configured to, after the laser treatment of the eye of the current patient t:

include the set of adjusted intended refractive corrections to be applied to the eye of the current patient in the sets of intended refractive corrections to be applied to eyes of previous patients; and include the set of measured induced refractive corrections for the eye of the current patient as a result of the laser treatment in the sets of measured surgery induced refractive corrections of the eyes of the previous patients from the previous surgeries on the eyes of the previous patients.

26. The system of claim 23, wherein a plurality of values of the set of adjusted intended refractive corrections to be applied to the eye of the current patient are each altered by a plurality of values of the effective treatment function.

* * * * *